(12) United States Patent
Brew et al.

(10) Patent No.: US 9,849,110 B2
(45) Date of Patent: Dec. 26, 2017

(54) INTERMITTENT FIBRATE ADMINISTRATION METHOD

(71) Applicant: Biocopea Limited, London (GB)

(72) Inventors: John Brew, Hertfordshire (GB); Robin Mark Bannister, Essex (GB)

(73) Assignee: Biocopea Limited, London (GB)

( * ) Notice: Subject to any disclaimer, the term of this patent is extended or adjusted under 35 U.S.C. 154(b) by 0 days.

(21) Appl. No.: 15/365,423

(22) Filed: Nov. 30, 2016

(65) Prior Publication Data

US 2017/0079951 A1 Mar. 23, 2017

Related U.S. Application Data

(63) Continuation of application No. 14/061,880, filed on Oct. 24, 2013, now Pat. No. 9,539,240.

(60) Provisional application No. 61/718,110, filed on Oct. 24, 2012.

(51) Int. Cl.
| | |
|---|---|
| *A61K 31/192* | (2006.01) |
| *A61K 31/216* | (2006.01) |
| *A61K 31/405* | (2006.01) |
| *A61K 31/351* | (2006.01) |
| *A61K 31/40* | (2006.01) |
| *A61K 45/06* | (2006.01) |
| *A61K 31/19* | (2006.01) |
| *A61K 31/202* | (2006.01) |
| *A61K 31/22* | (2006.01) |
| *A61K 31/366* | (2006.01) |
| *A61K 31/4406* | (2006.01) |
| *A61K 31/4418* | (2006.01) |
| *A61K 31/47* | (2006.01) |
| *A61K 31/505* | (2006.01) |
| *A61K 9/00* | (2006.01) |
| *G09B 5/00* | (2006.01) |

(52) U.S. Cl.
CPC .......... *A61K 31/405* (2013.01); *A61K 9/0053* (2013.01); *A61K 31/19* (2013.01); *A61K 31/192* (2013.01); *A61K 31/202* (2013.01); *A61K 31/22* (2013.01); *A61K 31/351* (2013.01); *A61K 31/366* (2013.01); *A61K 31/40* (2013.01); *A61K 31/4406* (2013.01); *A61K 31/4418* (2013.01); *A61K 31/47* (2013.01); *A61K 31/505* (2013.01); *A61K 45/06* (2013.01); *G09B 5/00* (2013.01)

(58) Field of Classification Search
None
See application file for complete search history.

*Primary Examiner* — Theodore R West
(74) *Attorney, Agent, or Firm* — Entralta P.C.; Annette S. Parent; Peter D. Weinstein

(57) ABSTRACT

The present specification discloses compositions comprising a pharmaceutical composition to reduce or maintain LDL and/or cholesterol levels in an individual and a plurality of therapeutic compounds to increase or maintain HDL levels in an individual. The present specification also discloses a treatment protocol wherein a pharmaceutical composition is administered to an individual on a schedule wherein the pharmaceutical composition is provided for a period of time and then not provided to the individual and this treatment protocol is repeated for the term of the individual's treatment.

20 Claims, No Drawings

INTERMITTENT FIBRATE ADMINISTRATION METHOD

This application is a continuation that claims the benefit of priority pursuant to 35 U.S.C. 120 to U.S. Non-Provisional patent application Ser. No. 14/061,880, filed Oct. 24, 2013, a patent application that claims the benefit of priority pursuant to 35 U.S.C. 119(e) to U.S. Provisional Patent Application 61/718,110, filed Oct. 24, 2012, the content of each of which is hereby incorporated by reference in its entirety.

INTRODUCTION

Statins, fibrates niacin, omega-3 fatty acids and other therapeutic compounds are commonly prescribed for patients suffering from high levels of low density lipoproteins ("LDL"), which is associated with high levels of cholesterol and a greater probability of suffering from cardiovascular disease. Statins, fibrates niacin, omega-3 fatty acids and other therapeutic compounds are also commonly prescribed for patients suffering from low levels of high density lipoproteins ("HDL"). Most treatments using statins, fibrates, niacin, omega-3 fatty acids and other therapeutic compounds require the patient to take the therapeutic on a daily basis. With the number of patients being prescribed statins, fibrates, niacin, omega-3 fatty acids and other therapeutic compounds increasing yearly as the benefits of these therapeutic compounds are recognized, the cost to public health organizations, private insurance companies and other payers of health care costs continues to increase, causing each a financial strain on government budgets and the budgets of private payers.

Statins are an important class of therapeutic compounds used to lower LDL and/or cholesterol, which are associated with an increase in cardiovascular disease. Statins are also associated with an increase in the levels of high density lipoproteins (HDL), which have been shown to improve clinical outcomes in cardiovascular patients. As a result of the benefits seen from the use of statins, for instance, in cardiovascular patients who see an improvement in prognosis, this category of therapeutic compounds is very widely prescribed. With increased generic availability of statins their use is likely to expand further.

Statins act by competitively inhibiting HMG-CoA reductase, the first committed enzyme of the HMG-CoA reductase pathway, which plays a central role in the production of cholesterol in the liver. Because statins are similar to HMG-CoA on a molecular level they take the place of HMG-CoA in the enzyme and reduce the rate by which it is able to produce meylonate, the next molecule in the cascade that eventually produces cholesterol, as well as a number of other compounds. This ultimately reduces cholesterol via several mechanisms.

Statins have been prescribed to over 127 million US cardiovascular patients. (Health, United States, 2010). A high proportion of statin use is also found in surveys of statin users outside the United States. The best-selling statin is atorvastatin, marketed as Lipitor (manufactured by Pfizer) and Torvast. By 2003 atorvastatin became the best-selling pharmaceutical in history, with Pfizer reporting sales of US$12.4 billion in 2008. As of 2010, a number of statins were on the market: atorvastatin (Lipitor and Torvast), fluvastatin (Lescol), lovastatin (Mevacor, Altocor, Altoprev), pitavastatin (Livalo, Pitava), pravastatin (Pravachol, Selektine, Lipostat), rosuvastatin (Crestor) and simvastatin (Zocor, Lipex).

While statins have been shown to have significant benefits, individuals taking them can suffer adverse side effects. Some individuals on statin therapy report myalgias, muscle cramps, or, less frequently, gastrointestinal or other symptoms. Liver enzyme derangements, typically in about 0.5% of individuals taking statins, are also seen at similar rates with placebo use and repeated enzyme testing, and generally return to normal either without discontinuance over time or after briefly discontinuing the drug. In randomized trials, statins increased the risk of an adverse effect by 39% compared to placebo (odds ratios 1.4); two-thirds of these were myalgia or raised liver enzymes with serious adverse effects similar to placebo. However, reliance on clinical trials can be misleading indications of real-world adverse effects—for example, the statin cerivastatin was withdrawn from the market in 2001 due to cases of rhabdomyolysis (muscle breakdown), although rhabdomyolysis did not occur in a meta-analysis of cerivastatin clinical trials. Other possible adverse effects include cognitive loss, neuropathy, pancreatic and hepatic dysfunction, and sexual dysfunction. Multiple other side effects occur rarely; typically also at similar rates with only placebo in the large statin safety/efficacy trials. Two randomized clinical trials found cognitive issues while two did not; recurrence upon reintroduction suggests these are causally related to statins in some individuals. A Danish case-control study published in 2002 suggested a relationship between long-term statin use and increased risk of nerve damage or polyneuropathy, but suggested this side effect is "rare, but it does occur" other researchers have pointed to studies of the effectiveness of statins in trials involving 50,000 people which have not shown nerve damage as a significant side effect.

Another element of the use of statins is cost. Daily administration of statins, although relatively low in cost per individual (between £100 and £400/patient/year), this is a clear financial burden on public, private and other providers of healthcare with over 4 million patients in the UK on statins. This financial burden is even greater in the United States and in poorer countries where healthcare provisions can be rudimentary.

A second group of therapeutics that are capable of reducing cholesterol levels are the fibrates, which constitute a class of amphipathic carboxylic acids. Fibrates are commonly used for a range of metabolic disorders, mainly hypercholesterolemia (high cholesterol), and are therefore hypolipidemic agents. Fibrates are used in accessory therapy in many forms of hypercholesterolemia, usually in combination with statins. Clinical trials have been used to support their use as monotherapy agents. Fibrates reduce the number of non-fatal heart attacks, but do not improve all-cause mortality and are therefore generally indicated for those not tolerant to statins.

Although less effective in lowering LDL than statins, fibrates improve HDL and triglyceride levels by increasing HDL levels and decreasing triglyceride levels. Fibrates activate peroxisome proliferator-activated receptors ("PPAR"), especially PPARα. The PPARs are a class of intracellular receptors that modulate carbohydrate and fat metabolism and adipose tissue differentiation. Activating PPARs induces the transcription of a number of genes that facilitate lipid metabolism. Fibrates are structurally and pharmacologically related to the thiazolidinediones, a novel class of anti-diabetic drugs that also act on PPARs (more specifically PPARγ).

Niacin is another therapeutic that is capable of reducing cholesterol levels. Niacin is a lipoprotein synthesis inhibitor that lowers triglyceride levels and slows removal of HDL, the "good" cholesterol. Niacin binds to and stimulates a G-protein-coupled receptor, GPR109A, which causes the inhibition of fat breakdown in adipose tissue. When administered to an individual, niacin decreases production of very low-density lipoprotein, or VLDL, which converts into LDL, thereby resulting in lower LDL levels. Lipids that are liberated from adipose tissue are normally used to build very-low-density lipoproteins (VLDL) in the liver, which are precursors of low-density lipoprotein (LDL) or "bad" cholesterol. Because niacin blocks the breakdown of fats, it causes a decrease in free fatty acids in the blood and, as a consequence, decreases the secretion of VLDL and cholesterol by the liver. By lowering VLDL levels, niacin also increases the level of high-density lipoprotein (HDL) or "good" cholesterol in blood, and therefore it is sometimes prescribed for people with low HDL, who are also at high risk of a heart attack.

Omega-3 fatty acids (also called ω-3 fatty acids or n-3 fatty acids) are fats commonly found in marine and plant oils. They are polyunsaturated fatty acids with a double bond (C═C) starting after the third carbon atom from the end of the carbon chain. The fatty acids have two ends—the acid (COON) end and the methyl (CH3) end. The location of the first double bond is counted from the methyl end, which is also known as the omega (ω) end or the n end. Omega-3 fatty acids are known to lower triglyceride and LDL levels.

Statins are known to not only affect HMG coA reductase inhibition, which reduces de novo synthesis of cholesterol, but statins affect the phenotype of macrophages. In this regard, statins help macrophages control lipid homeostasis via an alternative pathway (Nugy et al. 2012), as well as modulating the immune system. (Zeiser et al., 2008). These two functions are thought to be linked. (Hong and Tontonoz, 2009). When activated the macrophage has a central role in mounting an immune response against pathogens but is also activated in patients with high cholesterol levels, particularly high LDL levels. In patients with poor diet (high carbohydrate and high saturated fat) macrophages respond to this high stress environment by differentiating to an M1 phenotype (Bhargava and Lee, 2012). Statins induce long term phenotypic changes in M1 macrophages, allowing continued control of lipid homeostasis, as differentiated macrophages have a lifespan of several weeks. These changes include CD36 (lipoprotein transporter) up-regulation, PPAR gamma activation, induction of M2 macrophages and HDL secretion. Thus, due to the central role of macrophages in immune and cholesterol homeostasis, a long lasting effect in cholesterol management can be achieved with pulsatile statin therapy. As a result, statins can be administered on a periodic basis, limiting drug burden to individuals taking the therapeutic, resulting in a reduction in the likelihood of side effects and reducing the cost burden to the public or private payer.

Through our understanding of the immune system we believe we have defined a new protocol for limiting the side effects and drug burden of statin therapy. This protocol will substantially reduce the cost of statin, fibrates, niacin, omega-3 fatty acids and other therapeutic compounds capable of reducing or maintaining LDL levels and/or cholesterol levels in an individual. This protocol will also substantially reduce the cost of statin, fibrates, niacin, omega-3 fatty acids and other therapeutic compounds capable of increasing or maintaining HDL levels in an individual. With the side effects, costs and other liabilities associated with the regular use, and commonly daily use of statins, fibrates, niacin, omega-3 fatty acids and other therapeutic compounds that reduce or maintain LDL and/or cholesterol levels and/or increasing or maintaining HDL levels in an individual, there exists a need for a periodic therapeutic regimen that reduces the potential for side effects, reduces cost and other liabilities associated with regular use.

SUMMARY

Aspects of the present specification disclose a method for reducing or maintaining LDL and/or cholesterol and/or increasing or maintaining HDL levels in an individual, with the method comprising the step of administering a pharmaceutical composition to the individual for a first period of time followed by a period of time where the pharmaceutical composition is not administered to the individual and wherein the the pharmaceutical composition comprises one or more therapeutic compounds. Further aspects of the present specification disclose that an individual is administered a pharmaceutical composition over a period of time, wherein a period of administration is followed by a period where the pharmaceutical composition is not administered, which is followed by another period of administration that is followed by a period where the pharmaceutical composition is not administered and this treatment protocol is repeated for the duration of the individuals treatment.

Aspects of the present specification disclose a therapeutic compound that includes, without limitation, a statin, a fibrate, niacin or an omega-3 fatty acid, wherein the statin can include, without limitation, Atorvastatin, Cerivastatin, Fluvastatin, Lovastatin, Mevastatin, Pitavastatin, Pravastatin, Rosuvastatin or Simvastatin or any combination thereof and the fibrate can include, without limitation, Bezafibrate, Ciprofibrate, Clofibrate, Gemfibrozil or Fenofibrate or any combination thereof and the omega-3 fatty acid includes, without limitation, fish oils, algal oil, squid oil, and some plant oils such as echium oil and flaxseed oil or any combination thereof.

Aspects of the present specification also disclose a method, wherein a therapeutic compound is selected from an extended release, sustained release, long acting, immediate release, slow release or controlled release and wherein, the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration. The therapeutic compound is also released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration and wherein, a therapeutic compound is released over a period of about 1 day after administration, about 2 days after administration, about 3 days after administration, about 4 days after administration, about 5 days after administration, about 6 days after administration or about 7 days or more after administration.

Further aspects of the present specification disclose that a therapeutic compound is capable of reducing or maintaining LDL and/or cholesterol levels in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% and a therapeutic compound is capable of reducing or maintaining LDL and/or cholesterol levels in an individual by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Further aspects of the present specification disclose a therapeutic compound is capable of increasing or maintaining HDL levels in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% and wherein, a therapeutic compound is capable of increasing or maintaining HDL levels in an individual by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Aspects of the present specification disclose that a first period during which a therapeutic compound is administered to a patient is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more and wherein, a second period during which treatment with a therapeutic compound is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Aspects of the present specification disclose that a therapeutic compound is administered to an individual by inhalation, topically, intranasally, orally, sublingual, intravenously, rectally, vaginally, or subcutaneously. Further aspects of the present specification disclose that at a dose in the range of about 0.001 mg/kg/day to about 100 mg/kg/day and wherein, a therapeutic compound is administered to an individual at a dose in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day and wherein, a therapeutic compound is administered to an individual at a dose in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

Aspects of the present specification disclose that a therapeutic compound is administered to an individual at a dose in the range of about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day and wherein, a therapeutic compound is administered to an individual at a dose in the range of about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day and wherein, a therapeutic compound is administered to an individual at a dose in the range of 1 mg/day to about 3,000 mg/day. In aspects of this embodiment, an effective amount of a therapeutic compound disclosed herein may be, e.g., at least 1 mg/day, at least 5 mg/day, at least 10 mg/day, at least 15 mg/day, at least 20 mg/day, at least 25 mg/day, at least 30 mg/day, at least 40 mg/day, at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day.

Aspects of the present specification disclose that a therapeutic compound is administered to an individual at a dose in the range of 1 mg/day to about 1 mg/day to about 1,000 mg/day, about 5 mg/day to about 1,000 mg/day, about 10 mg/day to about 1,000 mg/day, about 15 mg/day to about 1,000 mg/day, about 20 mg/day to about 1,000 mg/day, about 25 mg/day to about 1,000 mg/day, about 30 mg/day to about 1,000 mg/day, about 40 mg/day to about 1,000 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day and wherein, a therapeutic compound is a statin administered to an individual at a dose in the range of 0.001 mg/kg/day to about 100 mg/kg/day and wherein, a therapeutic compound is a statin administered to an individual at a dose in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a statin disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day and wherein, a therapeutic compound is a statin administered to an individual at a dose in the range of about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day and wherein, a therapeutic compound is a statin administered to an individual at a dose in the range of a about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day and wherein, a therapeutic compound is a statin administered to an individual at a dose in the range of about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day and wherein, a therapeutic compound is a statin administered to an individual at a dose in the range of about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day and wherein, a. therapeutic compound is a statin administered to an individual at a dose in the range of about 1 mg/day to about 3,000 mg/day.

Aspects of the present specification disclose that a therapeutic compound is a statin administered to an individual at a dose in the range of at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day and wherein, a therapeutic compound is a statin administered to an individual at a dose in the range of about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

Aspects of the present specification disclose that a therapeutic compound is a fibrate administered to an individual at a dose in the range of 0.001 mg/kg/day to about 100 mg/kg/day and wherein, a therapeutic compound is a fibrate administered to an individual at a dose in the range of at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day and wherein, a therapeutic compound is a fibrate administered to an individual at a dose in the range of about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

Aspects of the present specification disclose that a therapeutic compound is administered to an individual as a single dosage or cumulative dosage.

Aspects of the present specification disclose that a therapeutic compound is provided in a kit and wherein, a kit includes the therapeutic compound and instructions for use.

Aspects of the present specification disclose that a therapeutic compound is provided in a package, wherein, without limitation the package is selected from a container, bottle, tube, a blister pack or a canister.

Aspects of the present specification disclose that an individual is notified to resume administration of a therapeutic compound following a period where the therapeutic compound was not administered to the individual, wherein an individual is notified, without limitation, by email, text, instant messaging, telephone call, postal mail or overnight express delivery service.

Aspects of the present specification disclose that an individual administered a therapeutic compound maintains LDL and cholesterol level. Further aspects of the present specification disclose that an individual administered a therapeutic compound maintains HDL level.

Further aspects of the present specification disclose the use of a composition in the manufacture of a medicament for the reduction or maintenance of LDL levels. Additional aspects of the present specification disclose the use of a composition in the manufacture of a medicament for the reduction or maintenance of cholesterol levels. Additional aspects of the present specification disclose the use of a composition in the manufacture of a medicament for the increase or maintenance of HDL levels.

Aspects of the present specification disclose the use of a composition in the manufacture of a medicament wherein the administration of a pharmaceutical composition is to treat cardiovascular disease and wherein, the cardiovascular disease includes, without limitation, a heart failure, a pulmonary infarction, or an aortic aneurysm.

Aspects of the present specification disclose a composition comprising a pharmaceutical composition to reduce or maintain LDL and/or cholesterol levels in an individual, wherein the pharmaceutical composition is administered to the individual for a first period of time followed by a period where the pharmaceutical composition is not administered to the individual. Further aspects of the present specification disclose a composition wherein the individual is administered a pharmaceutical composition over a period of time, wherein a period of administration is followed by a period where the pharmaceutical composition is not administered and the period of administration followed by a period where the pharmaceutical composition is not administered and this treatment protocol is repeated for the duration of the individuals treatment.

Aspects of the present specification disclose a composition, wherein the pharmaceutical composition comprises one or more therapeutic compounds and wherein, a therapeutic compound is a statin, a fibrate, niacin or an omega-3 fatty acid or any combination thereof. Aspects of the present specification disclose a statin is selected from Atorvastatin, Cerivastatin, Fluvastatin, Lovastatin, Mevastatin, Pitavastatin, Pravastatin, Rosuvastatin or Simvastatin or any combination thereof and wherein, a fibrate is selected from Bezafibrate, Ciprofibrate, Clofibrate, Gemfibrozil or Fenofibrate or any combination thereof and wherein, an omega-3 fatty acid is selected from fish oils, algal oil, squid oil, and some plant oils such as echium oil and flaxseed oil or any combination thereof.

DESCRIPTION

The present specification discloses various therapeutic compounds that reduce or maintain LDL and/or cholesterol levels in an individual. Consequently, a considerably reduced dose of a therapeutic compound can be given for an equivalent effect for each individual therapeutic compound, thereby reducing side-effects, costs and other issues related to the use of statins, fibrates, niacin, omega-3 fatty acids and other therapeutic compounds capable of reducing or maintaining LDL and/or cholesterol levels.

The present specification discloses various therapeutic compounds that increase or maintain HDL levels that are administered on a periodic schedule. Consequently, a considerably reduced dose of a therapeutic compound can be given for an equivalent effect for each individual therapeutic compound, thereby reducing side-effects, costs and other issues related to the use of statins, fibrates, niacin, omega-3 fatty acids and other therapeutic compounds capable increasing or maintaining HDL levels in an individual taking such therapeutic compound.

While the ability to administer statins, fibrates, niacin, omega-3 fatty acids and other therapeutic compounds capable of reducing or maintaining LDL and/or cholesterol levels on a periodic schedule can result from different mechanisms, one mechanism that allows such periodic dosing is related to the activation of macrophages in individuals, including, without limitation, individuals suffering from cardiovascular disease. In support of this finding, the present inventors determined that PPARγ stimulating drugs have a long duration of activity in inflamed individuals (rheumatoid arthritis and osteoarthritis), with 1 week worth of treatment lasting for more than 1 month (data not shown). A similar result is expected following administration of statins, fibrates, niacin, omega-3 fatty acids and other therapeutic compounds capable of reducing or maintaining LDL or cholesterol levels on PPARγ and its modulation of macrophage phenotype, lipid homeostasis and immunity, will also produce a long term effect. Evidence for the modulation of the lipid related immune system by statins is clear and can be found in the following: statins increase PPAR gamma activity through COX-2 induction, through the production of 15d-PGJ2 (Yano et al, 2007); statins induce CD36 expression in monocytes, through an inhibition of Rho GTPases (Ruiz-Velasco et al., 2004); and, statins induce macrophages to secrete HDL (Argmann et al., 2005).

While the ability to administer statins, fibrates, niacin, omega-3 fatty acids and other therapeutic compounds capable of reducing or maintaining HDL levels on a periodic schedule can result from different mechanisms, one mechanism that allows such periodic dosing is related to the activation of macrophages in individuals, including, without limitation, individuals suffering from cardiovascular disease. In support of this finding, the present inventors determined that PPARγ stimulating drugs have a long duration of activity in inflamed individuals (rheumatoid arthritis and osteoarthritis), with 1 week worth of treatment lasting for more than 1 month (data not shown). A similar result is expected following administration of statins, fibrates, niacin, omega-3 fatty acids and othertherapeutic compounds capable of reducing or maintaining HDL levels on PPARγ and its modulation of macrophage phenotype, lipid homeostasis and immunity, will also produce a long term effect. Evidence for the modulation of the lipid related immune system by statins is clear and can be found in the following: statins increase PPAR gamma activity through COX-2 induction, through the production of 15d-PGJ2 (Yano et al, 2007); statins induce CD36 expression in monocytes, through an inhibition of Rho GTPases (Ruiz-Velasco et al., 2004); and, statins induce macrophages to secrete HDL (Argmann et al., 2005).

PPARγ induction has two key effects in macrophages; firstly it induces apoptosis of M1 macrophages (Chinetti et al., 1998). The resultant apoptotic bodies then cause surrounding macrophages to differentiate to M2 phenotype (Ariel and Serhan, 2012). Secondly, PPARγ induction can also directly cause M1 macrophages to differentiate into M2 macrophages (Bouhlel et al., 2007). Once matured, macrophages have a life span over several weeks (Parihar et al., 2010). As a result, statin, fibrates, niacin, omega-3 fatty acids and other therapeutic compounds capable of reducing or maintaining LDL and/or cholesterol levels induce mature macrophages with an M2 phenotype, which are able to effectively regulate lipid homeostasis over a long time period. Supporting this hypothesis, the up-regulation of CD36 has also been associated with the M2 phenotype (Oh et al., 2012). These factors together indicate that statins, fibrates, niacin, omega-3 fatty acids and other therapeutic compounds capable of reducing and/or maintaining LDL and cholesterol levels can continue to control LDL and/or cholesterol levels, long after the statin therapy has been ceased. The result is that statins, fibrates, niacin, omega-3 fatty acids and other therapeutic compounds capable of reducing and or maintaining LDL and or cholesterol levels can be administered periodically.

Aspects of the present specification disclose, in part, a pharmaceutical composition. As used herein, the term "pharmaceutical composition" is synonymous with "pharmaceutically acceptable composition" and refers to a therapeutically effective concentration of an active ingredient, such as, e.g., any of the therapeutic compounds disclosed herein. As used herein, the term "pharmaceutically acceptable" refers to any molecular entity or composition that does not produce an adverse, allergic or other untoward or unwanted reaction when administered to an individual. A pharmaceutical composition disclosed herein is useful for medical and veterinary applications. A pharmaceutical composition may be administered to an individual alone, or in combination with other supplementary active ingredients, agents, therapeutic compounds or hormones.

A pharmaceutical composition disclosed herein may comprise one or more therapeutic compounds disclosed herein. In one embodiment, pharmaceutical composition disclosed herein may comprise only a single a therapeutic compound capable of reducing or maintaining LDL and/or cholesterol levels in an individual, at least two therapeutic compounds capable of reducing or maintaining LDL and/or cholesterol levels in an individual. In another embodiment, pharmaceutical composition disclosed herein may comprise a plurality of therapeutic compounds capable of reducing or maintaining LDL and/or cholesterol levels in an individual. In aspects of this embodiment, a pharmaceutical composition disclosed herein comprises at least one therapeutic compound capable of reducing or maintaining LDL and/or cholesterol levels in an individual, at least two therapeutic compounds capable of reducing and/or maintaining LDL and/or cholesterol levels in an individual, or at least four therapeutic compounds capable of reducing or maintaining LDL and/or cholesterol levels in an individual, a pharmaceutical composition disclosed herein comprises at most two therapeutic compounds capable of reducing or maintaining LDL and/or cholesterol levels in an individual, or at most four therapeutic compounds capable of reducing or maintaining LDL and/or cholesterol levels in an individual. In yet other aspects of this embodiment, a pharmaceutical composition disclosed herein comprises one to three therapeutic compounds capable of reducing or maintaining LDL and/or cholesterol levels in an individual, two to five therapeutic compounds capable of reducing and/or maintaining LDL and/or cholesterol levels in an individual, three to five therapeutic compounds capable of reducing or maintaining LDL and/or cholesterol levels in an individual, or two to three therapeutic compounds capable of reducing and/or maintaining LDL and/or cholesterol levels in an individual. In aspects of this embodiment, a therapeutic compound capable of reducing or maintaining LDL and/or cholesterol levels in an individual includes, without limitation, a statin, fibrates, niacin, omega-3 fatty acids and other therapeutic compounds capable of reducing or maintaining LDL and/or cholesterol levels in an individual.

A pharmaceutical composition disclosed herein may comprise one or more therapeutic compounds disclosed herein. In one embodiment, pharmaceutical composition disclosed herein may comprise only a single a therapeutic compound capable of increasing or maintaining HDL levels in an individual, at least two therapeutic compounds capable of increasing or maintaining HDL levels in an individual. In another embodiment, pharmaceutical composition disclosed herein may comprise a plurality of therapeutic compounds capable of increasing or maintaining HDL levels in an individual. In aspects of this embodiment, a pharmaceutical composition disclosed herein comprises at least one therapeutic compound capable of increasing or maintaining HDL levels in an individual, at least two therapeutic compounds capable of increasing or maintaining HDL levels in an individual, or at least four therapeutic capable of increasing or maintaining HDL levels in an individual, a pharmaceutical composition disclosed herein comprises at most two therapeutic compounds capable of increasing or maintaining HDL levels in an individual, or at most four therapeutic compounds capable of increasing and/or maintaining HDL levels in an individual. In yet other aspects of this embodiment, a pharmaceutical composition disclosed herein comprises one to three therapeutic compounds capable of increasing or maintaining HDL levels in an individual, two to five therapeutic compounds capable of increasing or maintaining HDL levels in an individual, three to five therapeutic compounds capable of increasing or maintaining HDL levels in an individual, or two to three therapeutic compounds capable of increasing or maintaining HDL levels in an individual. In aspects of this embodiment, a therapeutic compound capable of increasing or maintaining HDL levels in an individual includes, without limitation, a statin, fibrates, niacin, omega-3 fatty acids and other therapeutic compounds capable of increasing or maintaining HDL levels in an individual.

In another embodiment, a pharmaceutical composition disclosed herein comprises including, without limitation, a statin, fibrates, niacin, omega-3 fatty acids and other therapeutic compounds capable of reducing and/or maintaining LDL and/or cholesterol levels in an individual and a single additional therapeutic compound including, without limitation, a statin, fibrates, niacin, omega-3 fatty acids and other therapeutic compounds capable of reducing or maintaining LDL and/or cholesterol levels in an individual. In another embodiment, a pharmaceutical composition disclosed herein comprises including, without limitation, a statin, fibrates, niacin, omega-3 fatty acids and other therapeutic compounds capable of reducing and/or maintaining LDL and/or cholesterol levels in an individual and a plurality of additional therapeutic compound including, without limitation, a statin, fibrates, niacin, omega-3 fatty acids and other therapeutic compounds capable of reducing and/or maintaining LDL and/or cholesterol levels in an individual. In aspects of this embodiment, a pharmaceutical composition disclosed herein comprises including, without limitation, a statin, fibrates, niacin, omega-3 fatty acids and other therapeutic compounds capable of reducing and/or maintaining LDL and/or cholesterol levels in an individual and at least one additional therapeutic compound a statin, fibrates, niacin, omega-3 fatty acids and other therapeutic compounds capable of reducing and/or maintaining LDL and/or cholesterol levels in an individual, at least two additional therapeutic compounds including, without limitation, a statin, fibrates, niacin, omega-3 fatty acids and other therapeutic compounds capable of reducing and/or maintaining LDL and/or cholesterol levels in an individual, at least three additional therapeutic compounds including, without limitation, including, without limitation, a statin, fibrates, niacin, omega-3 fatty acids and other therapeutic compounds capable of reducing and/or maintaining LDL and/or cholesterol levels in an individual, at least four additional therapeutic compounds capable of reducing and/or maintaining LDL and/or cholesterol levels in an individual. In other aspects of this embodiment, a pharmaceutical composition disclosed herein comprises a including, without limitation, a statin, fibrates, niacin, omega-3 fatty acids and other therapeutic compounds capable of reducing and/or maintaining LDL and/or cholesterol levels in an individual and at most one additional therapeutic compound including, without limitation, a statin, fibrates, niacin, omega-3 fatty acids and other therapeutic compounds capable of reducing and/or maintaining LDL and/or cholesterol levels in an individual, at most two additional therapeutic compounds including, without limitation, a statin, fibrates, niacin, omega-3 fatty acids and other therapeutic compounds capable of reducing and/or maintaining LDL and/or cholesterol levels in an individual, at most three additional therapeutic compounds capable of reducing and/or maintaining LDL and/or cholesterol levels in an individual, at most four additional therapeutic compounds including, without limitation, a statin, fibrates, niacin, omega-3 fatty acids and other therapeutic compounds capable of reducing and/or maintaining LDL and/or cholesterol levels in an individual. In yet other aspects of this embodiment, a pharmaceutical composition disclosed herein comprises including, without limitation, a statin, fibrates, niacin, omega-3 fatty acids and other therapeutic compounds capable of reducing and/or maintaining LDL and/or cholesterol levels in an individual and one to three additional therapeutic compounds including, without limitation, a statin, fibrates, niacin, omega-3 fatty acids and other therapeutic compounds capable of reducing and/or maintaining LDL and/or cholesterol levels in an individual, two to four additional therapeutic compound including, without limitation, a statin, fibrates, niacin, omega-3 fatty acids and other therapeutic compounds capable of reducing and/or maintaining LDL and/or cholesterol levels in an individual, two to three additional therapeutic compounds including, without limitation, a statin, fibrates, niacin, omega-3 fatty acids and other therapeutic compounds capable of reducing and/or maintaining LDL and/or cholesterol levels in an individual, two to five additional therapeutic compound including, without limitation, a statin, fibrates, niacin, omega-3 fatty acids and other therapeutic compounds capable of reducing and/or maintaining LDL and/or cholesterol levels in an individual, or three to five additional therapeutic compound including, without limitation, a statin, fibrates, niacin, omega-3 fatty acids and other therapeutic compounds capable of reducing and/or maintaining LDL and/or cholesterol levels in an individual. In aspects of this embodiment, an additional therapeutic compound including, without limitation, a statin, fibrates, niacin, omega-3 fatty acids and other therapeutic compounds capable of reducing and/or maintaining LDL and/or cholesterol levels in an individual.

In another embodiment, a pharmaceutical composition disclosed herein comprises including, without limitation, a statin, fibrates, niacin, omega-3 fatty acids and other therapeutic compounds capable of increasing or maintaining HDL levels in an individual and a single additional therapeutic compound including, without limitation, a statin, fibrates, niacin, omega-3 fatty acids and other therapeutic compounds capable of increasing or maintaining HDL levels in an individual. In another embodiment, a pharmaceutical composition disclosed herein comprises including, without limitation, a statin, fibrates, niacin, omega-3 fatty acids and other therapeutic compounds capable of increasing or maintaining HDL levels in an individual and a plurality of additional therapeutic compound including, without limitation, a statin, fibrates, niacin, omega-3 fatty acids and other therapeutic compounds capable of increasing or maintaining HDL levels in an individual. In aspects of this embodiment, a pharmaceutical composition disclosed herein comprises including, without limitation, a statin, fibrates, niacin, omega-3 fatty acids and other therapeutic compounds capable of increasing or maintaining HDL levels in an individual and at least one additional therapeutic compound a statin, fibrates, niacin, omega-3 fatty acids and other therapeutic compounds capable of increasing or maintaining HDL levels in an individual, at least two additional therapeutic compounds including, without limitation, a statin, fibrates, niacin, omega-3 fatty acids and other therapeutic compounds capable of increasing or maintaining HDL levels in an individual, at least three additional therapeutic compounds including, without limitation, including, without limitation, a statin, fibrates, niacin, omega-3 fatty acids and other therapeutic compounds capable of increasing or maintaining HDL levels in an individual, at least four additional therapeutic compounds capable of increasing or maintaining HDL levels in an individual. In other aspects of this embodiment, a pharmaceutical composition disclosed herein comprises a including, without limitation, a statin, fibrates, niacin, omega-3 fatty acids and other therapeutic compounds capable of increasing or maintaining HDL levels in an individual and at most one additional therapeutic compound including, without limitation, a statin, fibrates, niacin, omega-3 fatty acids and other therapeutic compounds capable of increasing or maintaining HDL levels in an individual, at most two additional therapeutic compounds including, without limitation, a statin, fibrates, niacin, omega-3 fatty acids and other therapeutic compounds capable of increasing or maintaining HDL levels in an individual, at most three additional therapeutic compounds capable of increasing or maintaining HDL levels in an individual, at most four additional therapeutic compounds including, without limitation, a statin, fibrates, niacin, omega-3 fatty acids and other therapeutic compounds capable of increasing or maintaining HDL levels in an individual. In yet other aspects of this embodiment, a pharmaceutical composition disclosed herein comprises including, without limitation, a statin, fibrates, niacin, omega-3 fatty acids and other therapeutic compounds capable of increasing or maintaining HDL levels in an individual and one to three additional therapeutic compounds including, without limitation, a statin, fibrates, niacin, omega-3 fatty acids and other therapeutic compounds capable of increasing or maintaining HDL levels in an individual, two to four additional therapeutic compound including, without limitation, a statin, fibrates, niacin, omega-3 fatty acids and other therapeutic compounds capable of increasing or maintaining HDL levels in an individual, two to three additional therapeutic compounds including, without limitation, a statin, fibrates, niacin, omega-3 fatty acids and other therapeutic compounds capable of increasing or maintaining HDL levels in an individual, two to five additional therapeutic compound including, without limitation, a statin, fibrates, niacin, omega-3 fatty acids and other therapeutic compounds capable of increasing or maintaining HDL levels in an individual, or three to five additional therapeutic compound including, without limitation, a statin, fibrates, niacin, omega-3 fatty acids and other therapeutic compounds capable of increasing or maintaining HDL levels in an individual. In aspects of this embodiment, an additional therapeutic compound including, without limitation, a statin, fibrates, niacin, omega-3 fatty acids and other therapeutic compounds capable of increasing or maintaining HDL levels in an individual.

In another embodiment, a pharmaceutical composition disclosed herein comprises a statin and a plurality of therapeutic compounds including, without limitation, a fibrate, niacin, omega-3 fatty acids and other therapeutic compounds capable of reducing and/or maintaining LDL and/or cholesterol levels in an individual disclosed herein, wherein the plurality of therapeutic compounds does not include a statin disclosed herein. In an aspect of this embodiment, a pharmaceutical composition disclosed herein comprises a methylxanthine and a plurality of therapeutic compounds capable of reducing and/or maintaining LDL and/or cholesterol levels in an individual, wherein the plurality of therapeutic compounds does not include Azatadine, Bromodiphenhydramine, Brompheniramine, Carbinoxamine, Cetirizine, Chlorpheniramine, Clemestine, Dexchlorpheniramine, Dexbrompheniramine, Diphenhydramine, Doxylamine, Pyrilamine, Tripelennamine, or Tripolidine.

In another embodiment, a pharmaceutical composition disclosed herein comprises a statin and a plurality of therapeutic compounds including, without limitation, a fibrate, niacin, omega-3 fatty acids and other therapeutic compounds capable of increasing or maintaining HDL levels in an individual disclosed herein, wherein the plurality of therapeutic compounds does not include a statin disclosed herein. In an aspect of this embodiment, a pharmaceutical composition disclosed herein comprises a methylxanthine and a plurality of therapeutic compounds capable of increasing or maintaining HDL levels in an individual, wherein the plurality of therapeutic compounds does not include Azatadine, Bromodiphenhydramine, Brompheniramine, Carbinoxamine, Cetirizine, Chlorpheniramine, Clemestine, Dexchlorpheniramine, Dexbrompheniramine, Diphenhydramine, Doxylamine, Pyrilamine, Tripelennamine, or Tripolidine.

A pharmaceutical composition disclosed herein may reduce an unwanted side effect elicited by administration of one or more of the therapeutic compounds contained in the pharmaceutical composition. Examples of unwanted side effects, include, without limitation, myalgias, muscle cramps, gastrointestinal, liver enzyme derangements or other side effects.

A pharmaceutical composition disclosed herein is beneficial for the treatment of cardiovascular disease. In an embodiment, a cardiovascular disease includes, without limitation, heart failure, pulmonary infarction and aortic aneurysm.

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. Any suitable form of a therapeutic compound may be chosen. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein may also be provided as prodrug or active metabolite.

A therapeutic compound disclosed herein may be a statin. As used herein, the term statin refers to a class of therapeutic compounds that include, without limitation, therapeutic compounds that are able to inhibit HMG-CoA reductase. Examples of suitable statins include, without limitation, Atorvastatin, Cerivastatin, Fluvastatin, Lovastatin, Mevastatin, Pitavastatin, Pravastatin, Rosuvastatin, Simvastatin.

A therapeutic compound disclosed herein may be a fibrate. As used herein, the term fibrate refers to a class of therapeutic compounds that include, without limitation, therapeutic compounds that are cholesterol-lowering drugs that are primarily effective in lowering triglycerides and, to a lesser extent, in increasing HDL-cholesterol levels. Examples of suitable fibrates include, without limitation, Bezafibrate, Ciprofibrate, Clofibrate, Gemfibrozil, Fenofibrate.

A therapeutic compound disclosed herein may be a statin in combination with one or more other therapeutic compounds. Examples of suitable statin combination pharmaceutical compositions include, without limitation, Advicor (lovastatin/niacin), Caduet® (amlodipine and atorvastatin), Juvisync® (sitagliptin/simvastatin), Simcor® (niacin extended-release/simvastatin).

A therapeutic compound disclosed herein may be a niacin. As used herein, the term niacin refers to a class of therapeutic compounds that include, without limitation, therapeutic compounds that Niacin, a B vitamin nicotinic acid. Examples of suitable niacin include, without limitation, Niaspan, Sio-Niacin, Nicotinic Acid, Niacor.

A therapeutic compound disclosed herein may be a niacin with one or more additional therapeutic compounds. Examples of suitable niacin combination pharmaceutical compositions, include, without limitation, 3 Vit Plus Niacinamide, Folic Acid, Vit B12, Vit C; Sarvear Pharmaceuticals Injection Aciplex Niacinamide, Pyridoxine, Riboflavin, Thiamine; Acichem Laboratories Capsule Aloederm Niacinamide, Aloe Vera, Sesame Oil, Vit E; Fem Care Pharma Limited Cream Amycobal C Folic Acid, Mecobalamin, Nicotinamide, Vit C; Ampus Life Sciences Ltd Injection Anizyme MPS Fungal Diastase, Nicotinamide, Papain, Simethicone; Anikem Laboratories Tablet Axtox Syr Cyanocobalamin, Lysine, Nicotinamide, Pyridoxine Allenge India Syrup B Folcin Niacinamide, Folic Acid, Riboflavin; West-Coast Pharmaceutical Works Tablet Becoshal Nicotinamide, Pyridoxine, Riboflavin, Thiamine; Shalina Laboratories Ltd Tablet Bigvin FC Niacinamide, Folic Acid, Mecobalamin, Vit C; Bestochem Formulations (India) Ltd. Injection Binicomplex Niacinamide, Vit B1, Vit B2; Bini Laboratories Pvt Ltd Tablet Bionery Mecobalamin, Nicotinamide, Pyridoxine; Invision Medi Sciences Injection Bitwel Niacinamide, Mecobalamin, Vit B6; Archicare Injection Bolovit-12 Niacinamide, Folic Acid, Vit B12, Vit C; Ultramark Healthcare Pvt Ltd. kit Bolovit-FC (Combi Pack) Niacinamide, Folic Acid, Mecobalamin, Vit C; Ultramark Healthcare Pvt Ltd. Injection Bolovit-FC Combipack Niacinamide, Folic Acid, Mecobalamin, Vit C; Bolcare Parenterals (Ultramark Healthcare Pvt Ltd) Bonrich Z Syr Calcium Gluconate, Cyanocobalamin, Vit B3, Zinc Sulphate; Invision Medi Sciences Syrup Carb XT Niacinamide, Folic Acid, Riboflavin; Iscon Lifesciences Capsule CB 12 Niacinamide, Folic Acid, Vit B12, Vit C; Mapra Laboratories Pvt Ltd. kit Cebeplex Niacinamide, Folic Acid, Vit B12, Vit C; Golden Pharmaceuticals India Pvt. Ltd. Injection Ciroplex Niacinamide, Pyridoxine, Riboflavin, Thiamine; Ciron Drugs & Pharmaceuticals Pvt Ltd Syrup Cubal-Plus Inj. Mecobalamin, Nicotinamide, Pyridoxine Hydrochloride; IP Cure Quick Remedies Injection Cymate Plus Niacinamide, Folic Acid, Methylcobalamin, Vit C; Cytochem Health Care (India) Pvt. Ltd. 1 kit Diacobal Forte Inj Niacinamide, Mecobalamin, Pyridoxine Mano; (Orchid Chemicals & Pharmaceuticals Ltd.) Injection Digiriv (60 ml) L-Ornithine-L Aspartate, Nicotinamide, Vit B2; East African (I) Remedies Pvt Ltd Syrup Ebexid B Nicotinamide, Pyridoxine, Thyroid; Svizera Healthcare (Maneesh Pharmaceuticals Ltd) Tablet Ecobal Inj Niacinamide, Folic Acid, Mecobalamin, Vit C; Forgo Pharmaceuticals (P) Ltd. 1kit Eldervit-12 Inj Niacinamide, Folic Acid, Vit B12, Vit C; Elder Pharmaceuticals Pvt Ltd kit Enerject 12 Niacinamide, Folic Acid, Vit B12, Vit C; Ankare (Anglo French Drugs & Industries Ltd) kit Exomega Niacinamide, Benzoic Acid, Phenoxyethanol; Piramal Healthcare Lotion Exomega (100 ml) Niacinamide, Benzoic Acid, Chlorphenesin, Phenoxyethanol; Piramal Healthcare Lotion Fiscovit C Niacinamide, Folic Acid, Methylcobalamin, Vit C; Ancalima Life Sciences Ltd. Injection Flovina Niacinamide, Folic Acid, Riboflavin; Sayona (Zota Healthcare Pvt Ltd) Tablet Foetop Niacinamide, Folic Acid IP; Pyridoxine Finecure Pharmaceuticals Ltd Tablet Folcin-12 Niacinamide, Folic Acid, Vit B12, Vit C; Unimarck Pharma (India) Limited Injection Folib Niacinamide, Folic Acid, Riboflavin; Que Pharma Pvt. Ltd Tablet Folicyn-12 Niacinamide, Folic Acid, Vit B12; Acron Pharmaceuticals Drops Folicyn-12 Niacinamide, Folic Acid, Vit B12, Vit B2; Acron Pharmaceuticals Tablet Folium Niacinamide, Folic Acid, Vit B13; Speciality Meditech Pvt. Ltd. Drops Folnet Niacinamide, Folic Acid, Riboflavin; Active Healthcare Tablet Folvina Niacinamide, Folic Acid, Riboflavin; Sayona (Zota Healthcare Pvt Ltd) Tablet Folwin Niacinamide, Folic Acid, Riboflavin; Mediwin Pharmaceuticals Tablet Folzin Niacinamide, Folic Acid, Riboflavin; Tunic Healthcare Tablet G Folvin Niacinamide, Folic Acid, Riboflavin; Shrinivas (Gujarat) Laboratories Pvt. Ltd. Tablet Gravoplex Niacinamide, Pyridoxine, Riboflavin, Thiamine; LA Grande (P) Ltd Capsule Heparek (60 ml) L-Ornithine L-Aspartate, Nicotinamide; Rekvina Pharmaceuticals India Pvt Ltd Syrup Hepasure (60 ml) L-Ornithine L-Aspartate, Nicotinamide, Riboflavin; Winsome Laboratories Ltd. Syrup Hepawin (60 ml) L-Ornithine L-Aspartate, Nicotinamide, Riboflavin; Waves Bio-Tech Pvt. Ltd. Syrup JP Tone Inj Methylcobalamin, Nicotinamide, Pyridoxine Hydrochloride IP; Jagsonpal Pharmaceuticals Ltd Injection L-Bex Forte Inj Niacinamide, Folic Acid, Methylcobalamin, Vit C; Lincoln Pharmaceuticals Ltd Injection Lenerve (2 ml) Benzyl Alcohol, Mecobalamin, Nicotinamide, Pyridoxine Hydrochloride IP HRD; Supra Healthcare Injection Livogard (60 ml) Niacinamide, L-Ornithine-L Aspartate, Riboflavin; Lark Laboratories (India) Ltd. Syrup Livogen Syr Liver Extract, Nicotinic Acid, Vit B1, Yeast; Allenburys (Glaxo Smithkline Pharmaceuticals Ltd.) Syrup Livogen Syr (120 ml) Liver Extract, Nicotinic Acid, Vit B1, Yeast; Allenburys (Glaxo Smithkline Pharmaceuticals Ltd.) Syrup Livopax L-ornithine-L-Aspartate, Nicotinamide, Vit B2; Baxter (India) Pvt. Ltd. Syrup Lornit Syrup L-Ornithine-L Aspartate, Nicotinamide, Riboflavin; Zuventus Health Care Ltd. Syrup Magvit M Niacinamide, Folic Acid, Mecobalamin, Vit C; Magnus Biotech Pvt. Ltd. Injection ME 12 Niacinamide, Mecobalamin, Vit B1; Archicare Injection Mecona Plus Niacinamide, Methylcobalamin, Pyridoxine; Hauz Pharma Pvt Ltd Injection Methovit Niacinamide, Folic Acid, Mecobalamin, Vit C; Mark Remedies (Glenmark Pharmaceuticals Ltd) Injection Mysulid Plus Niacinamide, Nimesulide, Paracetamol; New Gayzel Pharmaceuticals Tablet Mysulid Plus (60 ml) Niacinamide, Nimesulide, Paracetamol; New Gayzel Pharmaceuticals Suspension Neuro C Niacinamide, Folic Acid, Mecobalamin, Vit C; Arlak Biotech Pvt Ltd 1 kit Neuromind Plus Methylcobalamin, Nicotinamide, Pyridoxine; Health Biotech Pvt Ltd. Injection Nicinal Nicotinic Acid, Vit B6; Cipla Limited Tablet Nut Plus Niacinamide, Folic Acid, Mecobalamin, Vit C; Winsun Laboratories Injection Ornipan Syr L-ornithine-L-Aspartate, Nicotinamide, Riboflavin; Moraceae Pharmaceuticals (P) Ltd. Syrup P-Zyme Niacinamide, Fungal Diastase, Papain; Palas Pharmaceutical Pvt. Ltd Syrup Pepstaz MPS Fungal Diastase, Nicotinamide, Papain, Simethicone; Frank Medilink Tablet Ribonic Niacinamide, Folic Acid, Riboflavin; Agron Remedies Pvt Ltd Tablet; Sancovit Niacinamide, Folic Acid, Mecobalamin, Vit C; Sanjivani Parenteral Ltd Injection Sunmic Mecobalamin, Nicotinamide, Vit B6; Little Greave Pharmaceuticals Ltd. Injection Tecob Plus Niacinamide, Mecobalamin, Pyridoxine Hydrochloride IP; Zentis Drugs Pvt Ltd Injection Tobal Plus Mecobalamin, Nicotinamide, Pyridoxine; Injecto Capta Pvt. Ltd. Injection Unifol Injection Cyanocobalamin, Folic Acid, Nicotinamide; Unijules Life Sciences Ltd Injection Vibifol Niacinamide, Folic Acid, Riboflavin; Osho Pharma Pvt. Ltd. Tablet Visoliv L-Ornithine L-Aspartate, Nicotinamide, Riboflavin; Vision Biotech Syrup Vitamin-B Niacinamide, Vit B1, Vit B2; Cyper Pharma Tablet Vitcofol Drop Folic Acid, Nicotinamide, Vit B12; FDC Limited Drops Vitcofol Injection Niacinamide, Folic Acid, Vit B14; FDC Limited Injection Vitcofol-C Niacinamide, Folic Acid, Vit B12, Vit C; Proxima (FDC Limited) Injection Zuvital Nicotinamide, Pyridoxine Hydrochloride IP Daksh (Zodak Pharmaceuticals) Syrup.

A therapeutic compound disclosed herein may be an omega-3 fatty acid with one or more additional therapeutic compounds. Examples of suitable omega-3 fatty acids include, without limitation, fish oils, algal oil, squid oil and some plant oils, such as, without limitation, echium oil and flaxseed oil.

Aspects of the present specification disclose, without limitation, a therapeutic compound is a long acting, sustained release, extended release, immediate release, slow release, or controlled release therapeutic compound and the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration or is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration or is released over a period of about 1 day after administration, about 2 days after administration, about 3 days after administration, about 4 days after administration, about 5 days after administration, about 6 days after administration or about 7 days or more after administration.

In an embodiment, a therapeutic compound delivery platform includes both a sustained release therapeutic compound delivery platform and an extended release therapeutic compound delivery platform. In an embodiment, the term "sustained release" refers to the release of a therapeutic compound or compounds disclosed herein over a period of about seven days or more. In an embodiment, the term "extended release" refers to the release of a therapeutic compound or compounds disclosed herein over a period of time of less than about seven days.

In an embodiment, the therapeutic compound includes, without limitation, an extended release, sustained release or long acting form. In an additional embodiment, the extended release, sustained release or long acting form of a therapeutic compound is linked, without limitation, to a polymer, including, without limitation, to a water soluble polymer. In an embodiment, a water-soluble polymer is selected, without limitation, from the group consisting of poly(alkylene oxide), poly(vinyl pyrrolidone), poly(vinyl alcohol), polyoxazoline, poly(acryloylmorpholine), and combinations thereof. In an additional embodiment, the water soluble polymer is a poly(alkylene oxide) such as, without limitation, a poly(ethylene glycol) derivative. In an embodiment, a water soluble polymer has, without limitation, a nominal average molecular weight in the range from about 2,000 Daltons to about 150,000 Daltons, from about 2,000 Daltons to about 125,000 Daltons, from about 2,000 Daltons to about 100,000 Daltons, from about 2,000 Daltons to about 75,000 Daltons, from about 2,000 Daltons to about 50,000 Daltons, from about 2,000 Daltons to about 25,000 Daltons, from about 5,000 Daltons to about 150,000 Daltons, from about 5,000 Daltons to about 100,000 Daltons, from about 5,000 Daltons to about 75,000 Daltons, from about 5,000 Daltons to about 50,000 Daltons, from about 5,000 Daltons to about 25,000 Daltons, from about 10,000 Daltons to about 100,000 Daltons, from about 10,000 Daltons to about 75,000 Daltons, from about 10,000 Daltons to about 50,000 Daltons, from about 10,000 Daltons to about 25,000 Daltons. In an embodiment, a water soluble polymer has, without limitation, a nominal average molecular weight of at least 150,000 Daltons, at least 125,000 Daltons, at least 100,000 Daltons, at least 75,000 Daltons, at least 50,000 Daltons, at least 25,000 Daltons. In an additional embodiment, the extended release, sustained release or long acting form of a therapeutic compound is linked, without limitation, to a polymer, including, without limitation, to a water soluble polymer through, without limitation, a stable linker or a releasable linker.

In one embodiment, a therapeutic compound disclosed herein is capable of reducing and/or maintaining LDL and/or cholesterol levels in an individual. In aspects of this embodiment, a therapeutic compound capable of reducing and/or maintaining LDL and/or cholesterol levels in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound capable of reducing and/or maintaining LDL and/or cholesterol levels in an individual by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In one embodiment, a therapeutic compound disclosed herein is capable of increasing or maintaining HDL levels in an individual. In aspects of this embodiment, a therapeutic compound capable of increasing or maintaining HDL levels in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound capable of increasing or maintaining HDL levels in an individual by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces LDL and/or cholesterol levels. In aspects of this embodiment, a therapeutic compound herein reduces LDL levels by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound herein reduces LDL levels by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein increases HDL levels. In aspects of this embodiment, a therapeutic compound increases HLD levels by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound increases HDL levels by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A therapeutic compound is administered to a patient for a period of time followed by a separate period of time where a therapeutic compound is not administered to a patient. In one embodiment, a cycle comprising a period of time where a therapeutic compound is administered to a patient followed by a separate period of time where a therapeutic compound is not administered to a patient may be conducted once. In another embodiment, a cycle comprising a period of time where a therapeutic compound is administered to a patient followed by a separate period of time where a therapeutic compound is not administered to a patient may be conducted a plurality of times. In aspects of this embodiment, a cycle comprising a period of time where a therapeutic compound is administered to a patient followed by a separate period of time where a therapeutic compound is not administered to a patient may be conducted, e.g., at least 2 times, at least 3 times, at least 4 times, at least 5 times, at least 6 times, at least 7 times, at least 8 times, at least 9 times, at least 10 times, at least 12 times, at least 15 times, at least 18 times, at least 20 times, at least 25 times, or at least 30 times.

In another embodiment, the period of administration of a therapeutic compound followed by a period where administration is stopped is repeated for a determined or undetermined period of time. In aspects of this embodiment, a therapeutic compound is administered for a first period and a second period following the first period, with administration stopped during the second period. In aspects of this embodiment, a therapeutic compound is administered for a first period and a second period following the first period, with administration stopped during the second period, followed by a third period where administration of the therapeutic compound is started and then a fourth period following the third period where administration is stopped.

In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In an embodiment, a first therapeutic compound is administered to an individual and at a later date, a second therapeutic compound is administered to the same individual. In aspects of this embodiment, the first therapeutic compound is a statin and the second therapeutic compound is a fibrate, niacin or omega-3 fatty acid. In a further aspect of this embodiment, the first therapeutic compound is a fibrate and the second therapeutic compound is a statin, niacin or omega-3 fatty acid.

In an embodiment, a first therapeutic compound is administered to an individual at the same time as a second therapeutic compound is administered to the individual. In aspects of this embodiment, the first therapeutic compound is a statin and the second therapeutic compound is a fibrate, niacin or omega-3 fatty acid. In a further aspect of this embodiment, the first therapeutic compound is a fibrate and the second therapeutic compound is a statin, niacin or omega-3 fatty acid.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, flavoring agents, coloring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

A therapeutic compound disclosed herein, or a composition comprising such a therapeutic compound, may be formulated for either local or systemic delivery using topical, enteral or parenteral routes of administration. Additionally, a therapeutic compound disclosed herein may be formulated by itself in a pharmaceutical composition, or may be formulated together with one or more other therapeutic compounds disclosed herein in a single pharmaceutical composition.

A therapeutic compound disclosed herein, or a composition comprising such a therapeutic compound, may be made into an inhaled formulation. Inhaled formulations suitable for enteral or parenteral administration include, without limitation, aerosols, dry powders. A therapeutic compound or composition disclosed herein intended for such administration may be prepared according to any method known to the art for the manufacture of pharmaceutical compositions. In such inhaled dosage forms, the therapeutic compound may be prepared for delivery as an aerosol in a liquid propellant for use in a pressurised (PDI) or other metered dose inhaler (MDI). Propellants suitable for use in a PDI or MDI include, without limitation, CFC-12, HFA-134a, HFA-227, HCFC-22 (difluorochloromethane), HFA-152 (difluoroethane and isobutane). A therapeutic compound may also be delivered using a nebulisers or other aerosol delivery system. A therapeutic compound may be prepared for delivery as a dry powder for use in a dry powder inhaler (DPI). A dry powder for use in the inhalers will usually have a mass median aerodynamic diameter of less than 30 pm, preferably less than 20 pm and more preferably less than 10 pm. Microparticles having aerodynamic diameters in the range of about 5 pm to about 0.5 pm will generally be deposited in the respiratory bronchioles, whereas smaller particles, having aerodynamic diameters in the range of about 2 pm to about 0.05 pm, are likely to be deposited in the alveoli. A DPI may be a passive delivery mechanism, which relies on the individual's inspiration to introduce the particles into the lungs, or an active delivery mechanism, requiring a mechanism for delivering the powder to the individual. As disclosed herein, an equivalent reduction or maintenance of LDL and/or cholesterol in an individual requires only one-third the dose of a statin, fibrate, niacin and/or omega-3 fatty acids the same dose of a statin, fibrate, niacin and/or omega-3 fatty acids administered orally. As disclosed herein, an equivalent increase or maintenance of HDL in an individual requires only one-third the dose of a statin, fibrate, niacin and/or omega-3 fatty acids the same dose of a statin, fibrate, niacin and/or omega-3 fatty acids administered orally. In inhalatory formulations, a therapeutically effective amount of a therapeutic compound disclosed herein for an inhaled formulation may be between about 0.0001% (w/v) to about 60% (w/v), about 0.001% (w/v) to about 40.0% (w/v), or about 0.01% (w/v) to about 20.0% (w/v). In inhalatory formulations, a therapeutically effective amount of a therapeutic compound disclosed herein for an inhaled formulation may also be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a solid formulation. Solid formulations suitable for enteral or parenteral administration include, without limitation, capsules, tablets, pills, troches, lozenges, powders and granules suitable for inhalation or for reconstitution into sterile injectable solutions or dispersions. A therapeutic compound or composition disclosed herein intended for such administration may be prepared according to any method known to the art for the manufacture of pharmaceutical compositions. In such solid dosage forms, the therapeutic compound may be admixed with (a) at least one inert customary excipient (or carrier), such as, e.g., sodium citrate or dicalcium phosphate or (b) fillers or extenders, as for example, starch, lactose, sucrose, glucose, mannitol, isomalt, and silicic acid, (c) binders, such as, e.g., carboxymethylcellulose, alignates, gelatin, polyvinylpyrrolidone, sucrose and acacia, (d) humectants, such as, e.g., glycerol, (e) disintegrating agents, such as, e.g., agar-agar, calcium carbonate, corn starch, potato starch, tapioca starch, alginic acid, certain complex silicates and sodium carbonate, (f) solution retarders, such as, e.g., paraffin, (g) absorption accelerators, such as, e.g., quaternary ammonium compounds, (h) wetting agents, such as, e.g., cetyl alcohol and glycerol monostearate, (i) adsorbents, such as, e.g., kaolin and bentonite, (j) lubricants, such as, e.g., talc, stearic acid, calcium stearate, magnesium stearate, solid polyethylene glycols, sodium lauryl sulfate or mixtures thereof, and (k) buffering agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In solid formulations, a therapeutically effective amount of a therapeutic compound disclosed herein typically may be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a semi-solid formulation. Semi-solid formulations suitable for topical administration include, without limitation, ointments, creams, salves, and gels. A therapeutic compound or composition disclosed herein intended for such administration may be prepared according to any method known to the art for the manufacture of pharmaceutical compositions. In semi-solid formulations, a therapeutically effective amount of a therapeutic compound disclosed herein typically may be between about 0.0001% (w/v) to about 60% (w/v), about 0.001% (w/v) to about 40.0% (w/v), or about 0.01% (w/v) to about 20.0% (w/v). In semi-solid formulations, a therapeutically effective amount of a therapeutic compound disclosed herein typically may also be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a liquid formulation. Liquid formulations suitable for enteral or parenteral administration include, without limitation, solutions, syrups, elixirs, dispersions, emulsions, and suspensions. A therapeutic compound or composition disclosed herein intended for such administration may be prepared according to any method known to the art for the manufacture of pharmaceutical compositions. In such liquid dosage forms, a therapeutic compound or composition disclosed herein may be admixed with (a) suitable aqueous and nonaqueous carriers, (b) diluents, (c) solvents, such as, e.g., water, ethanol, propylene glycol, polyethyleneglycol, glycerol, vegetable oils, such as, e.g., rapeseed oil and olive oil, and injectable organic esters such as ethyl oleate; and/or fluidity agents, such as, e.g., surfactants or coating agents like lecithin. In the case of dispersions and suspensions, fluidity can also be controlled by maintaining a particular particle size. In liquid formulations, a therapeutically effective amount of a therapeutic compound disclosed herein typically may be between about 0.0001% (w/v) to about 60% (w/v), about 0.001% (w/v) to about 40.0% (w/v), or about 0.01% (w/v) to about 20.0% (w/v).

Syrups and elixirs may be formulated with sweetening agents, for example glycerol, propylene glycol, sorbitol or sucrose. Such formulations may also contain a demulcent, a preservative, flavoring agents, and coloring agents.

Liquid suspensions may be formulated by suspending a therapeutic compound disclosed herein in admixture with excipients suitable for the manufacture of aqueous suspensions. Such excipients are suspending agents, for example sodium carboxymethylcellulose, methylcellulose, hydroxypropylmethylcellulose, sodium alginate, pectin, polyvinyl pyrrolidone, polyvinyl alcohol, natural gum, agar, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate.

Oily suspensions may be formulated by suspending a therapeutic compound disclosed herein in admixture with (a) vegetable oils, such as, e.g., almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof, (b) a saturated fatty acid, an unsaturated fatty acid, or a combination thereof, such as, e.g., palmitic acid, stearic acid, oleic acid, linoleic acid, linolenic acid, or a combination thereof, (c) mineral oil such as, e.g., liquid paraffin, (d) surfactants or detergents. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the combined therapeutic compounds in admixture with a dispersing or wetting agent, suspending agent and one or more preservatives.

A therapeutic compound disclosed herein may be in the form of oil-in-water emulsions. The oily phase may be a vegetable oil as disclosed herein or a mineral oil as disclosed herein or mixtures thereof. Suitable emulsifying agents may be naturally occurring gums, such as, e.g., gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

A therapeutic compound disclosed herein, or a composition comprising such a therapeutic compound, may also be incorporated into a therapeutic compound delivery platform in order to achieve a controlled release profile over time. Such a therapeutic compound delivery platform comprises a therapeutic compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the therapeutic compound delivery platform. Examples of biodegradable, bioerodible, and/or bioresorbable polymers and methods useful to make a therapeutic compound delivery platform are described in, e.g., Drost, et. al., Controlled Release Formulation, U.S. Pat. No. 4,756,911; Smith, et. al., Sustained Release Drug Delivery Devices, U.S. Pat. No. 5,378,475; Wong and Kochinke, Formulation for Controlled Release of Drugs by Combining Hyrophilic and Hydrophobic Agents, U.S. Pat. No. 7,048,946; Hughes, et. al., Compositions and Methods for Localized Therapy of the Eye, U.S. Patent Publication 2005/0181017; Hughes, Hypotensive Lipid-Containing Biodegradable Intraocular Implants and Related Methods, U.S. Patent Publication 2005/0244464; Altman, et al., Silk Fibroin Hydrogels and Uses Thereof, U.S. Patent Publication 2011/0008437; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed therapeutic compound delivery platform depends on several factors. The more relevant factors in the selection of the appropriate polymer(s), include, without limitation, compatibility of polymer with a therapeutic compound, desired release kinetics of a therapeutic compound, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A therapeutic compound delivery platform includes both a sustained release therapeutic compound delivery platform and an extended release therapeutic compound delivery platform. As used herein, the term "sustained release" refers to the release of a therapeutic compound disclosed herein over a period of about seven days or more. As used herein, the term "extended release" refers to the release of a therapeutic compound disclosed herein over a period of time of less than about seven days.

In aspects of this embodiment, a sustained release therapeutic compound delivery platform releases a therapeutic compound disclosed herein with substantially zero order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release therapeutic compound delivery platform releases a therapeutic compound disclosed herein with substantially zero order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a sustained release therapeutic compound delivery platform releases a therapeutic compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release therapeutic compound delivery platform releases a therapeutic compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a therapeutic compound delivery platform releases a therapeutic compound disclosed herein with substantially zero order release kinetics over a period of, e.g., about 1 day after administration, about 2 days after administration, about 3 days after administration, about 4 days after administration, about 5 days after administration, or about 6 days after administration. In other aspects of this embodiment, a therapeutic compound delivery platform releases a therapeutic compound disclosed herein with substantially zero order release kinetics over a period of, e.g., at most 1 day after administration, at most 2 days after administration, at most 3 days after administration, at most 4 days after administration, at most 5 days after administration, or at most 6 days after administration.

In aspects of this embodiment, a therapeutic compound delivery platform releases a therapeutic compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a therapeutic compound delivery platform releases a therapeutic compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

Aspects of the present specification disclose, in part, reduction or maintenance of LDL and/or cholesterol levels in an individual. As used herein, the term "treating," refers to reduction or maintenance of LDL and/or cholesterol in an individual. For example, the term "treating" can mean reduction or maintenance of LDL and/or cholesterol levels in an individual by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with a high LDL and cholesterol levels are well known and can be determined by a person of ordinary skill in the art by using commonly known testing means, including blood tests. Those of skill in the art will know the appropriate symptoms or indicators associated with symptoms associated with a high LDL and cholesterol levels and will know how to determine if an individual is a candidate for treatment as disclosed herein.

Aspects of the present specification disclose, in part, increase or maintenance of HDL levels in an individual. As used herein, the term "treating," refers to increase or maintenance of HDL in an individual. For example, the term "treating" can mean r increase or maintenance of HDL levels in an individual by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with a low HDL levels are well known and can be determined by a person of ordinary skill in the art by using commonly known testing means, including blood tests. Those of skill in the art will know the appropriate symptoms or indicators associated with symptoms associated with a low HDL levels and will know how to determine if an individual is a candidate for treatment as disclosed herein.

A composition or compound is administered to an individual. An individual is typically a human being. Typically, any individual who is a candidate for treatment is a candidate with cardiovascular or other disease resultant from high levels of LDL and/or cholesterol or low levels of HDL as disclosed herein. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount", "effective dose", or "therapeutically effective dose" and when used in reference to reducing or maintaining LDL and/or cholesterol levels in an individual refers to the minimum dose of a therapeutic compound disclosed herein necessary to achieve the desired therapeutic effect and includes a dose sufficient to reduce or maintain LDL and/or cholesterol levels in an individual. The effectiveness of a therapeutic compound disclosed herein capable of reducing or maintaining LDL and/or cholesterol levels in an individual can be determined by observing an improvement in an individual based upon one or more clinical symptoms, and/or physiological indicators associated with reducing or maintaining LDL and/or cholesterol levels in an individual. An improvement in LDL and cholesterol levels also can be indicated by a reduced need for a concurrent therapy. The effectiveness of a therapeutic compound disclosed herein capable of increasing or maintaining HDL levels in an individual can be determined by observing an improvement in an individual based upon one or more clinical symptoms, and/or physiological indicators associated with an increase or maintaining HDL levels. An improvement in HDL levels also can be indicated by a reduced need for a concurrent therapy.

The appropriate effective amount of a therapeutic compound disclosed herein to be administered to reduce or maintain LDL and/or cholesterol levels in an individual condition can be determined by a person of ordinary skill in the art by taking into account factors, including, without limitation, the measured level of LDL and cholesterol in mg/dl in blood samples taken from the individual, the particular characteristics, history and risk factors of the patient, such as, e.g., age, weight, general health and the like, or any combination thereof. The appropriate effective amount of a therapeutic compound disclosed herein to be administered to increase or maintain HDL levels in an individual condition can be determined by a person of ordinary skill in the art by taking into account factors, including, without limitation, the measured level of HDL and cholesterol in mg/dl in blood samples taken from the individual, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans.

Wide variations in the necessary effective amount are to be expected in view of the differing efficiencies of the various routes of administration. For instance, oral administration of a therapeutic compound disclosed herein generally would be expected to require higher dosage levels than administration by inhalation. Similarly, systemic administration of a therapeutic compound disclosed herein would be expected to require higher dosage levels than a local administration. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors. One skilled in the art will recognize that the condition of the individual can be monitored throughout the course of therapy and that the effective amount of a therapeutic compound disclosed herein that is administered can be adjusted accordingly.

In an embodiment, in instances in which each of the therapeutic compounds themselves are administered, without limitation, as individual or separate dosage forms (e.g., capsules or tablets), the kit comprises, without limitation, each of the therapeutic compounds making up the composition of the invention, along with instructions for use. In an additional embodiment, the therapeutic compound components, without limitation, may be packaged in any manner suitable for administration, so long as the packaging, when considered along with the instructions for administration, without limitation, clearly indicates the manner in which each of the therapeutic compound components is to be administered. In a further embodiment, each of the therapeutic compounds or a combination of such therapeutic compounds may, without limitation, be combined into a single administrable dosage form such as a capsule, tablet, or other solid or liquid formulation. The therapeutic compound can be provided to an individual in a package. The package can be a container, for instance, without limitation, a bottle, a canister, a tube or other enclosed vessel. The package can also be a packet, such as a blister pack.

In an embodiment, the individual or separate dosage is in the form of a blister pack. In an aspect of this embodiment, a blister pack is a term for several types of pre-formed plastic packaging used for small consumer goods, foods, and for pharmaceuticals. In a further embodiment, a blister pack is comprised of a cavity or pocket made from a formable web, usually a thermoformed plastic and typically includes a backing of paperboard or a lidding seal of aluminum foil or plastic. In a further embodiment, a blister that folds onto itself is a clamshell. In an aspect of this embodiment, a blister pack is commonly used as unit-dose packaging for pharmaceutical tablets, capsules or lozenges. In an embodiment, a blister pack can provide barrier protection for shelf life requirements, and a degree of tamper resistance and can be used for packing physician samples of therapeutic compound products or for Over The Counter (OTC) products in the pharmacy.

In an embodiment, an individual is provided a treatment protocol wherein a pharmaceutical composition is administered on a periodic schedule, wherein the individual is informed by electronic notification to administer the therapeutic compound so that the individual is reminded to take the therapeutic compound on a period schedule. In an aspect of this embodiment, the electronic notification is by email, text, instant messaging or by another electronic notification method. In an embodiment, an individual is informed to administer the therapeutic compound on a period schedule through receipt of a telephone call, postal mail, overnight express (including, without limitation, FedEx and UPS) or other method of notification.

In aspects of this embodiment, a therapeutically effective amount of a therapeutic compound disclosed herein reduces or maintains LDL and/or cholesterol levels in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces or maintains LDL and/or cholesterol levels in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces or maintains LDL and/or cholesterol levels in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In aspects of this embodiment, a therapeutically effective amount of a therapeutic compound disclosed herein increases or maintains HDL levels in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein increases or maintains HDL levels in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein increases or maintains HDL levels in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In other aspects of this embodiment, a therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, a therapeutically effective amount of a therapeutic compound disclosed herein generally is in the range of about 1 mg/day to about 3,000 mg/day. In aspects of this embodiment, an effective amount of a therapeutic compound disclosed herein may be, e.g., at least 1 mg/day, at least 5 mg/day, at least 10 mg/day, at least 15 mg/day, at least 20 mg/day, at least 25 mg/day, at least 30 mg/day, at least 40 mg/day, at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day. In yet other aspects of this embodiment, an effective amount of a therapeutic compound disclosed herein may be between, e.g., about 1 mg/day to about 1,000 mg/day, about 5 mg/day to about 1,000 mg/day, about 10 mg/day to about 1,000 mg/day, about 15 mg/day to about 1,000 mg/day, about 20 mg/day to about 1,000 mg/day, about 25 mg/day to about 1,000 mg/day, about 30 mg/day to about 1,000 mg/day, about 40 mg/day to about 1,000 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

In other aspects of this embodiment, a therapeutically effective amount of a statin disclosed herein generally is in the range of about 0.001 mg/kg/day to about 100 mg/kg/day. In aspects of this embodiment, an effective amount of a statin disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a statin disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a statin disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a statin disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a statin disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a statin disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, a therapeutically effective amount of a statin disclosed herein generally is in the range of about 1 mg/day to about 3,000 mg/day. In aspects of this embodiment, an effective amount of a statin disclosed herein may be, e.g., at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day. In yet other aspects of this embodiment, an effective amount of a statin disclosed herein may be between, e.g., about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

In other aspects of this embodiment, a therapeutically effective amount of a fibrate disclosed herein generally is in the range of about 0.001 mg/kg/day to about 100 mg/kg/day. In aspects of this embodiment, an effective amount of a fibrate disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a fibrate disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a fibrate disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a fibrate disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a fibrate disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a fibrate disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, a therapeutically effective amount of a fibrate disclosed herein generally is in the range of about 1 mg/day to about 3,000 mg/day. In aspects of this embodiment, an effective amount of a statin disclosed herein may be, e.g., at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day. In yet other aspects of this embodiment, an effective amount of a fibrate disclosed herein may be between, e.g., about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

In other aspects of this embodiment, in conjunction with a statin, a therapeutically effective amount of a fibrate, niacin and/or omega-3 fatty acid disclosed herein generally is in the range of about 0.001 mg/kg/day to about 100 mg/kg/day. In aspects of this embodiment, in conjunction with a statin, a therapeutically effective amount of a fibrate, niacin and/or omega-3 fatty acid disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, in conjunction with a statin, a therapeutically effective amount of a fibrate, niacin and/or omega-3 fatty acid disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, in conjunction with a statin, a therapeutically effective amount of a fibrate, niacin and/or omega-3 fatty acid disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, in conjunction with a statin, a therapeutically effective amount of a fibrate, niacin and/or omega-3 fatty acid disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, in conjunction with a statin, a therapeutically effective amount of a fibrate, niacin and/or omega-3 fatty acid disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, in conjunction with a statin, a therapeutically effective amount of a fibrate, niacin and/or omega-3 fatty acid disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In aspects of this embodiment, in conjunction with a statin, a therapeutically effective amount of a fibrate, niacin and/or omega-3 fatty acid disclosed herein generally is in the range of about 1 mg/day to about 6,000 mg/day. In other aspects of this embodiment, in conjunction with a statin, a therapeutically effective amount of a fibrate, niacin and/or omega-3 fatty acid disclosed herein may be, e.g., at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, at least 3,000 mg/day, at least 3,500 mg/day, at least 4,000 mg/day, at least 4,500 mg/day, at least 5,000 mg/day, at least 5,500 mg/day, or at least 6,000 mg/day.

In yet other aspects of this embodiment, in conjunction with a statin, a therapeutically effective amount of a fibrate, niacin and/or omega-3 fatty acid disclosed herein may be between, e.g., about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, about 2,000 mg/day to about 3,000 mg/day, about 1,000 mg/day to about 4,000 mg/day, about 1,100 mg/day to about 4,000 mg/day, about 1,200 mg/day to about 4,000 mg/day, about 1,3000 mg/day to about 4,000 mg/day, about 1,400 mg/day to about 4,000 mg/day, about 1,500 mg/day to about 4,000 mg/day, about 1,600 mg/day to about 4,000 mg/day, about 1,700 mg/day to about 4,000 mg/day, about 1,800 mg/day to about 4,000 mg/day, about 1,900 mg/day to about 4,000 mg/day, about 2,000 mg/day to about 4,000 mg/day, about 2,500 mg/day to about 4,000 mg/day, about 3,000 mg/day to about 4,000 mg/day, about 1,000 mg/day to about 5,000 mg/day, about 1,100 mg/day to about 5,000 mg/day, about 1,200 mg/day to about 5,000 mg/day, about 1,3000 mg/day to about 5,000 mg/day, about 1,400 mg/day to about 5,000 mg/day, about 1,500 mg/day to about 5,000 mg/day, about 1,600 mg/day to about 5,000 mg/day, about 1,700 mg/day to about 5,000 mg/day, about 1,800 mg/day to about 5,000 mg/day, about 1,900 mg/day to about 5,000 mg/day, about 2,000 mg/day to about 5,000 mg/day, about 2,500 mg/day to about 5,000 mg/day, about 3,000 mg/day to about 5,000 mg/day, about 3,500 mg/day to about 5,000 mg/day, about 4,000 mg/day to about 5,000 mg/day, about 1,000 mg/day to about 6,000 mg/day, about 1,100 mg/day to about 6,000 mg/day, about 1,200 mg/day to about 6,000 mg/day, about 1,3000 mg/day to about 6,000 mg/day, about 1,400 mg/day to about 6,000 mg/day, about 1,500 mg/day to about 6,000 mg/day, about 1,600 mg/day to about 6,000 mg/day, about 1,700 mg/day to about 6,000 mg/day, about 1,800 mg/day to about 6,000 mg/day, about 1,900 mg/day to about 6,000 mg/day, about 2,000 mg/day to about 6,000 mg/day, about 2,500 mg/day to about 6,000 mg/day, about 3,000 mg/day to about 6,000 mg/day, about 3,500 mg/day to about 6,000 mg/day, about 4,000 mg/day to about 6,000 mg/day, about 4,500 mg/day to about 6,000 mg/day, or about 5,000 mg/day to about 6,000 mg/day.

Dosing can be single dosage or cumulative (serial dosing), and can be readily determined by one skilled in the art. For instance, reducing or maintaining LDL and/or cholesterol levels in an individual may comprise a one-time administration of an effective dose of a pharmaceutical composition disclosed herein. Alternatively, reducing or maintaining LDL and/or cholesterol levels in an individual may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Dosing can be single dosage or cumulative (serial dosing), and can be readily determined by one skilled in the art. For instance, increase or maintain HDL levels in an individual may comprise a one-time administration of an effective dose of a pharmaceutical composition disclosed herein. Alternatively, increase or maintain HDL levels in an individual may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Various routes of administration can be useful for administering a therapeutic compound disclosed herein, according to a method for reducing and/or maintaining LDL and/or cholesterol levels in an individual. Various routes of administration can be useful for administering a therapeutic compound disclosed herein, according to a method for increasing and/or maintaining HDL levels in an individual. A pharmaceutical composition may be administered to an individual by any of a variety of means depending, e.g., on the specific therapeutic compound or composition used, or other compound to be included in the composition, and the history, risk factors and symptoms of the individual. As such, topical, enteral or parenteral routes of administration may be suitable for reducing or maintaining LDL and/or cholesterol levels in an individual as disclosed herein and such routes include both local and systemic delivery of a therapeutic compound or composition disclosed herein. As such, topical, enteral or parenteral routes of administration may be suitable for increasing or maintaining HDL levels in an individual as disclosed herein and such routes include both local and systemic delivery of a therapeutic compound or composition disclosed herein. Compositions comprising either a single therapeutic compound disclosed herein, or two or more therapeutic compounds disclosed herein are intended for inhaled, topical, intranasal, oral, subcutaneous, sublingual, intravenous, rectal and/or vaginal use may be prepared according to any method known to the art for the manufacture of pharmaceutical compositions. A pharmaceutical composition disclosed herein can be administered to an individual in a single formulation or in separate formulations, for combined, simultaneous or sequential administration.

Aspects of the present specification may also be described as follows:
1. A method of reducing or maintaining LDL and/or cholesterol and/or increasing or maintaining HDL levels and/or treating a cardiovascular disease in an individual, the method comprising the step of administering a pharmaceutical composition to the individual for a first period of time followed by a period of time where the pharmaceutical composition is not administered to the individual.
2. The method according to embodiment 1, wherein the pharmaceutical composition comprises one or more therapeutic compounds.

3. The method according to embodiment 2, wherein the therapeutic compound is a statin, a fibrate, niacin or an omega-3 fatty acid.
4. The method according to embodiment 3, wherein the statin is selected from Atorvastatin, Cerivastatin, Fluvastatin, Lovastatin, Mevastatin, Pitavastatin, Pravastatin, Rosuvastatin or Simvastatin or any combination thereof.
5. The method according to embodiment 3, wherein the fibrate is selected from Bezafibrate, Ciprofibrate, Clofibrate, Gemfibrozil or Fenofibrate or any combination thereof.
6. The method according to embodiment 3, wherein the omega-3 fatty acid is selected from fish oils, algal oil, squid oil, and some plant oils such as echium oil and flaxseed oil or any combination thereof.
7. The method according to embodiment 3, wherein a therapeutic compound comprising niacin further comprises one or more therapeutic compounds.
8. The method according to any one of embodiments 1-7, wherein a therapeutic compound is selected from an extended release, sustained release, long acting, immediate release, slow release or controlled release.
9. The method according to any one of embodiments 1-8, wherein a therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.
10. The method according to any one of embodiments 1-8, wherein a therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration.
11. The method according to any one of embodiments 1-8, wherein a therapeutic compound is released over a period of about 1 day after administration, about 2 days after administration, about 3 days after administration, about 4 days after administration, about 5 days after administration, about 6 days after administration or about 7 days or more after administration.
12. The method according to any one of embodiments 1-11, wherein a therapeutic compound is capable of reducing LDL and/or cholesterol levels in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.
13. The method according to any one of embodiments 1-12, wherein a therapeutic compound is capable of reducing LDL and/or cholesterol levels in an individual by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.
14. The method according to any one of embodiments 1-11, wherein a therapeutic compound is capable of increasing HDL levels in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.
15. The method according to any one of embodiments 1-12, wherein a therapeutic compound is capable of increasing HDL levels in an individual by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.
16. The method according to any one of embodiments 1-15, wherein the first period of time is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.
17. The method according to embodiment 16, wherein the first period of time is for 7 days.
18. The method according to embodiment 16, wherein the first period of time is for 14 days.
19. The method according to any embodiments 1-18, wherein the second period of time is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.
20. The method according to embodiment 19, wherein the second period of time is for 7 days.
21. The method according to embodiment 19, wherein the second period of time is for 14 days.
22. The method according to embodiment 19, wherein the second period of time is for 21 days.
23. The method according to embodiment 19, wherein the second period of time is for 1 month.
24. The method according to embodiment 19, wherein the second period of time is for 12 months.
25. The method according to any one of embodiments 1-24, wherein the therapeutic compound is administered to an individual by inhalation, topically, intranasally, orally, sublingual, intravenously, rectally, vaginally, or subcutaneously.
26. The method according to any one of embodiments 1-25, wherein the therapeutic compound is administered to an individual at a dose in the range of about 0.001 mg/kg/day to about 100 mg/kg/day.

27. The method according to any one of embodiments 1-26, wherein the therapeutic compound is administered to an individual at a dose of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

28. The method according to any one of embodiments 1-27, wherein the therapeutic compound is administered to an individual at a dose in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

29. The method according to any one of embodiments 1-27, wherein the therapeutic compound is administered to an individual at a dose in the range of about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day.

30. The method according to any one of embodiments 1-27, wherein the therapeutic compound is administered to an individual at a dose in the range of about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

31. The method according to any of embodiments 1-25, wherein the therapeutic compound is administered to an individual at a dose in the range of 1 mg/day to about 3,000 mg/day.

32. The method according to any one of embodiments 1-25 and 31, wherein the therapeutic compound is administered to an individual at a dose in the range of 1 mg/day to about 1 mg/day to about 1,000 mg/day, about 5 mg/day to about 1,000 mg/day, about 10 mg/day to about 1,000 mg/day, about 15 mg/day to about 1,000 mg/day, about 20 mg/day to about 1,000 mg/day, about 25 mg/day to about 1,000 mg/day, about 30 mg/day to about 1,000 mg/day, about 40 mg/day to about 1,000 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

33. The method according to any one of embodiments 3, 4, or 8-25, wherein the therapeutic compound is a statin administered to an individual at a dose in the range of 0.001 mg/kg/day to about 100 mg/kg/day.

34. The method according to any one of embodiments 3, 4, 8-25, or 33, wherein the therapeutic compound is a statin administered to an individual at a dose of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a statin disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

35. The method according to any one of embodiments 3, 4, 8-25, or 33, wherein the therapeutic compound is a statin administered to an individual at a dose in a range of about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day.

36. The method according to any one of embodiments 3, 4, 8-25, or 33, wherein the therapeutic compound is a statin administered to an individual at a dose in a range of about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

37. The method according to any one of embodiments 3, 4, 8-25, or 33, wherein the therapeutic compound is a statin administered to an individual at a dose in a range of about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day.

38. The method according to any one of embodiments 3, 4, 8-25, or 33, wherein the therapeutic compound is a statin administered to an individual at a dose in a range of about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

39. The method according to any one of embodiments 3, 4, or 8-25, wherein the therapeutic compound is a statin administered to an individual at a dose in a range of about 1 mg/day to about 3,000 mg/day.

40. The method according to any one of embodiments 3, 4, 8-25, or 39, wherein the therapeutic compound is a statin administered to an individual at a dose in a range of at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day.

41. The method according to any one of embodiments 3, 4, 8-25, or 39, wherein the therapeutic compound is a statin administered to an individual at a dose in a range of about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

42. The method according to any one of embodiments 3, 5, or 8-25, wherein the therapeutic compound is a fibrate administered to an individual at a dose in a range of 0.001 mg/kg/day to about 100 mg/kg/day.

43. The method according to any one of embodiments 3, 5, 8-25, or 42, wherein the therapeutic compound is a fibrate administered to an individual at a dose in a range of at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day.

44. The method according to any one of embodiments 3, 5, 8-25, or 42, wherein the therapeutic compound is a fibrate administered to an individual at a dose in a range of about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

45. The method according to any one of embodiments 1-44, wherein the therapeutic compound is administered to an individual as a single dosage or cumulative dosage.

46. The method according to any one of embodiments 1-45, wherein the therapeutic compound is provided in a kit.

47. The method according to embodiment 46, wherein the kit includes the therapeutic compound and instructions for use.

48. The method according to embodiment 46, wherein the therapeutic compound is provided in a package, such as, e.g., a container, bottle, tube, a blister pack or a canister.

49. The method according to any one of embodiments 1-48, wherein an individual is notified to resume administration of a therapeutic compound following a period where the therapeutic compound was not administered to the individual.
50. The method according to embodiment 49, wherein the individual is notified by email, text, instant messaging, telephone call, postal mail or overnight express delivery service.
51. The method according to any one of embodiments 1-50, wherein a therapeutic compound is capable of maintaining LDL and cholesterol level.
52. The method according to any one of embodiments 1-50, wherein a therapeutic compound is capable of maintaining HDL level.
53. The method according to any one of embodiments 1-52, wherein the individual is administered a pharmaceutical composition over a period of time, wherein a period of administration is followed by a period where the pharmaceutical composition is not administered, which is followed by another period of administration that is followed by a period where the pharmaceutical composition is not administered and this treatment protocol is repeated for the duration of the individuals treatment.
54. The method according to any one of embodiments 1-53, wherein cardiovascular disease includes a heart failure, a pulmonary infarction, or an aortic aneurysm.
55. Use of a composition according to any one of embodiments 1-54 or 60-114 in the manufacture of a medicament for the reduction or maintenance of LDL levels and/or cholesterol levels.
56. Use of a composition according to any one of embodiments 1-54 or 60-114 in the manufacture of a medicament for the increase or maintenance of HDL levels.
57. Use of a composition according to any one of embodiments 1-54 or 60-114 in the manufacture of a medicament for the treatment of a cardiovascular disease.
58. The use according to any one of embodiments 1-54 or 60-114, wherein the administration of a pharmaceutical composition is to treat cardiovascular disease.
59. The use according to embodiment 57 or 58, wherein the cardiovascular disease includes a heart failure, a pulmonary infarction, or an aortic aneurysm.
60. A pharmaceutical composition to reduce or maintain LDL and/or cholesterol levels and/or increase or maintain HDL levels and/or treat a cardiovascular disease in an individual, wherein the pharmaceutical composition is administered to the individual for a first period of time followed by a period where the pharmaceutical composition is not administered to the individual.
61. The composition according to embodiment 60, wherein the individual is administered a pharmaceutical composition over a period of time, wherein a period of administration is followed by a period where the pharmaceutical composition is not administered and the period of administration followed by a period where the pharmaceutical composition is not administered and this treatment protocol is repeated for the duration of the individuals treatment.
62. The composition according to embodiment 60 or 61, wherein the pharmaceutical composition comprises one or more therapeutic compounds.
63. The composition according to embodiment 62, wherein the therapeutic compound is a statin, a fibrate, niacin or an omega-3 fatty acid.
64. The composition according to embodiment 63, wherein the statin is selected from Atorvastatin, Cerivastatin, Fluvastatin, Lovastatin, Mevastatin, Pitavastatin, Pravastatin, Rosuvastatin or Simvastatin or any combination thereof.
65. The composition according to embodiment 63, wherein the fibrate is selected from Bezafibrate, Ciprofibrate, Clofibrate, Gemfibrozil or Fenofibrate or any combination thereof.
66. The composition according to embodiment 63, wherein the omega-3 fatty acid is selected from fish oils, algal oil, squid oil, and some plant oils such as echium oil and flaxseed oil or any combination thereof.
67. The composition according to embodiment 63, wherein a therapeutic compound comprising niacin further comprises one or more therapeutic compounds.
68. The composition according to any one of embodiments 60-67, wherein a therapeutic compound is selected from an extended release, sustained release, long acting, immediate release, slow release or controlled release.
69. The composition according to any one of embodiments 60-67, wherein a therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.
70. The composition according to any one of embodiments 60-67, wherein a therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration.
71. The composition according to any one of embodiments 60-67, wherein a therapeutic compound is released over a period of about 1 day after administration, about 2 days after administration, about 3 days after administration, about 4 days after administration, about 5 days after administration, about 6 days after administration or about 7 days or more after administration.
72. The composition according to any one of embodiments 60-71, wherein a therapeutic compound is capable of reducing LDL and/or cholesterol levels in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.
73. The composition according to any one of embodiments 60-71, wherein a therapeutic compound is capable of reducing LDL and/or cholesterol levels in an individual by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

74. The composition according to any one of embodiments 60-71, wherein a therapeutic compound is capable of increasing HDL levels in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

75. The composition according to any one of embodiments 60-71, wherein a therapeutic compound is capable of increasing HDL levels in an individual by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

76. The composition according to any one of embodiments 60-75, wherein the first period of time is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

67. The composition according to embodiment 76, wherein the first period of time is for 7 days.

78. The composition according to embodiment 76, wherein the first period of time is for 14 days.

79. The composition according to any one of embodiments 60-78, wherein the second period of time is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

80. The composition according to embodiment 79, wherein the second period of time is for 7 days.

81. The composition according to embodiment 79, wherein the second period of time is for 14 days.

82. The composition according to embodiment 79, wherein the second period of time is for 21 days.

83. The composition according to embodiment 79, wherein the second period of time is for 1 month.

84. The composition according to embodiment 79, wherein the second period of time is for 12 months.

85. The composition according to any one of embodiments 60-84, wherein the therapeutic compound is administered to an individual by inhalation, topically, intranasally, orally, sublingual, intravenously, rectally, vaginally, or subcutaneously.

86. The composition according to any one of embodiments 60-85, wherein the therapeutic compound is administered to an individual at a dose in the range of about 0.001 mg/kg/day to about 100 mg/kg/day.

87. The composition according to any one of embodiments 60-86, wherein the therapeutic compound is administered to an individual at a dose of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

88. The composition according to any one of embodiments 60-86, wherein the therapeutic compound is administered to an individual at a dose in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

89. The composition according to any one of embodiments 60-86, wherein the therapeutic compound is administered to an individual at a dose in the range of about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day.

90. The composition according to any one of embodiments 60-86, wherein the therapeutic compound is administered to an individual at a dose in the range of about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

91. The composition according to any one of embodiments 60-85, wherein the therapeutic compound is administered to an individual at a dose of 1 mg/day to about 3,000 mg/day.

92. The composition according to any one of embodiments 60-85 or 91, wherein the therapeutic compound is administered to an individual at a dose in the range of 1 mg/day to about 1 mg/day to about 1,000 mg/day, about 5 mg/day to about 1,000 mg/day, about 10 mg/day to about 1,000 mg/day, about 15 mg/day to about 1,000 mg/day, about 20 mg/day to about 1,000 mg/day, about 25 mg/day to about 1,000 mg/day, about 30 mg/day to about 1,000 mg/day, about 40 mg/day to about 1,000 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

93. The composition according to any one of embodiments 63, 64, or 68-85, wherein the therapeutic compound is a statin administered to an individual at a dose in the range of 0.001 mg/kg/day to about 100 mg/kg/day.

94. The composition according to any one of embodiments 63, 64, 68-85, or 93, wherein the therapeutic compound is a statin administered to an individual at a dose of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a statin disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

95. The composition according to any one of embodiments 63, 64, 68-85, or 93, wherein the therapeutic compound is a statin administered to an individual at a dose in the range of about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day.

96. The composition according to any one of embodiments 63, 64, 68-85, or 93, wherein the therapeutic compound is a statin administered to an individual at a dose in the range of about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

97. The composition according to any one of embodiments 63, 64, 68-85, or 93, wherein the therapeutic compound is a statin administered to an individual at a dose in the range of about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day.

98. The composition according to any one of embodiments 63, 64, 68-85, or 93, wherein the therapeutic compound is a statin administered to an individual at a dose in the range of about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

99. The composition according to any one of embodiments 63, 64, or 68-85, wherein the therapeutic compound is a statin administered to an individual at a dose in the range of about 1 mg/day to about 3,000 mg/day.

100. The composition according to any one of embodiments 63, 64, 68-85, or 99, wherein the therapeutic compound is a statin administered to an individual at a dose in the range of at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day.

101. The composition according to any one of embodiments 63, 64, 68-85, or 99, wherein the therapeutic compound is a statin administered to an individual at a dose in the range of about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

102. The composition according to any one of embodiments 63, 65, or 68-85, wherein the therapeutic compound is a fibrate administered to an individual at a dose in the range of 0.001 mg/kg/day to about 100 mg/kg/day.

103 The composition according to any one of embodiments 63, 65, 68-85 or 102, wherein the therapeutic compound is a fibrate administered to an individual at a dose in the range of at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day.

104. The composition according to any one of embodiments 63, 65, 68-85 or 102, wherein the therapeutic compound is a fibrate administered to an individual at a dose in the range of about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

105. The composition according to any one of embodiments 60-104, wherein the therapeutic compound is administered to an individual as a single dosage or cumulative dosage.

106. The composition according to any one of embodiments 60-105, wherein the therapeutic compound is provided in a kit.

107. The composition according to embodiment 106, wherein the kit includes the therapeutic compound and instructions for use.

108. The composition according to embodiment 106, wherein the therapeutic compound is provided in a package.

109. The composition according to embodiment 107, wherein the package is selected from a bottle, a blister pack or a canister.

110. The composition according to any one of embodiments 60-109, wherein an individual is notified to resume administration of a therapeutic compound following a period where the therapeutic compound was not administered to the individual.

111. The composition according to embodiment 110, wherein the individual is notified by email, text, instant messaging, telephone call, postal mail or overnight express delivery service.

112. The composition according to any one of embodiments 60-111, wherein a therapeutic compound is capable of maintaining LDL and cholesterol level.

113. The composition according to any one of embodiments 60-111, wherein a therapeutic compound is capable of maintaining HDL level.

114. The composition according to any one of embodiments 60-113, wherein cardiovascular disease includes a heart failure, a pulmonary infarction, or an aortic aneurysm.

115. The method according to any one of embodiments 1-54, wherein the step of administering a pharmaceutical composition to the individual for a first period of time followed by a period of time where the pharmaceutical composition is not administered to the individual is repeated at least 2 times, at least 3 times, at least 4 times, at least 5 times, at least 6 times, at least 7 times, at least 8 times, at least 9 times, at least 10 times, at least 12 times, at least 15 times, at least 18 times, at least 20 times, at least 25 times, or at least 30 times.

116. A kit for reducing or maintaining LDL and/or cholesterol and/or increasing or maintaining HDL levels and/or treating a cardiovascular disease in an individual, the kit comprising a pharmaceutical composition as defined in any one of embodiments 60-114 and instructions for use, wherein the instructions provide for the administration of the pharmaceutical composition to the individual for a first period of time followed by a period where the pharmaceutical composition is not administered to the individual.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods or uses of reducing or maintaining LDL and/or cholesterol levels in an individual or treating a cardiovascular disease.

Example 1

Periodic Treatment with a Statin

A 67 year old male with a family history of cardiovascular disease is provided a routine history and physical examination by a physician. During the physical examination, the 67 year old male has blood drawn and his LDL, HDL and cholesterol levels tested. Normal levels have been established as LDL: 100 mg/dl to 129 mg/dl; HDL: greater than 40 mg/dl; total cholesterol: less than 200 mg/dl; and, triglycerides: 100 mg/dl to 150 mg/dl. The results of the test show that the 67 year old man has LDL level of 89 mg/dl, HDL level of 28 mg/dl and a cholesterol level of 254 mg/dl. The physician prescribes simvastatin at an initial daily dose of 20 mg taken orally daily. The 67 year old man returns to the physician for a follow on blood test six months later and he is found to have LDL level of 110 mg/dl, HDL level of 48 mg/dl and a cholesterol level of 172 mg/dl. At this point the physician changes the frequency of dosing to one week taking simvastatin at a dose of 20 mg followed by a week off where he does not take simvastatin, then a week taking simvastatin and then a week off. The patient repeats this administration procedure for a period of six months. To ensure compliance, the physician sets up a service to call the man to remind him to take the simvastatin every other week. Six months later, the man returns to the physician for a blood test. The results of the test show that he has an LDL level of 111 mg/dl, HDL level of 48 mg/dl and a cholesterol level of 165 mg/dl. At this point the physician changes the frequency of dosing to one week taking simvastatin at a dose of 20 mg followed by two weeks off, then a week taking simvastatin and then two weeks off. The service that calls the man to remind him to take the simvastatin is set to call him every two weeks to comply with the new dosing regimen. Six months later the man returns to the physician for a blood test. The results of the test show that he has an LDL level of 115 mg/dl, HDL level of 48 mg/dl and a cholesterol level of 162 mg/dl. At this point the physician changes the frequency of dosing to one week taking simvastin at a dose of 20 mg followed by a month off and this pattern of administration, a week taking simvastatin followed by a month off is repeated. To ensure compliance, the physician sets the service to call the man to remind him to take the simvastin once a month. Six months later the man returns to the physician for a blood test. The results of the test show that he has an LDL level of 114 mg/dl, HDL level of 48 mg/dl and a cholesterol level of 160 mg/dl. Six months later the man returns to the physician for a blood test. The results of the test show that he has an LDL level of 115 mg/dl, HDL level of 48 mg/dl and a cholesterol level of 161 mg/dl. The man continues taking the simvastin for a week followed by a month off for the rest of his life, with his LDL levels ranging from 113-118, HDL levels ranging from 45-51 and his cholesterol levels ranging from 155-173. Based on these results, the once monthly administration of simvastin was successful at maintaining normal levels of LDL, HDL and cholesterol.

Example 2

Periodic Treatment with a Statin

A 45 year old male visits his physician and during the visit undergoes a blood test. The man is found to have an LDL level of 92 mg/dl, HDL level of 41 mg/dl and a cholesterol level of 212 mg/dl. The physician prescribes atorvastatin at an initial dose of 40 mg taken orally for one week followed by a month off where he does not take atorvastatin followed by a week of taking atorvastatin and then another month off on a repeating schedule. To remind the man to take atorvastatin after the monthly breaks, he downloads an application to his smart phone and inputs the first day he is to take atorvastatin and the application automatically determines the day a month after stopping taking atorvastatin that he is to start taking the atorvastatin again. A month after taking the first weeks dose of atorvastatin, the man receives a reminder from the application on his smart phone to take the second dose of atorvastatin. This repeats on a monthly basis. The 45 year old man returns to the physician for a follow on blood test six months later and he is found to have LDL level of 120 mg/dl, HDL level of 45 mg/dl and a cholesterol level of 161 mg/dl. At this point the physician changes the frequency of the breaks between week of dosing to every two months, while maintaining the dose of 20 mg. The man inputs the new schedule into the application on his smart phone and he is reminded to take atorvastatin every two month by the application. Six months later, the man returns to the physician for a blood test. The results of the test show that he has an LDL level of 120 mg/dl, HDL level of 48 mg/dl and a cholesterol level of 160 mg/dl. The physician recommends that the man continue to take atorvastatin for a week followed by a two month break, which the man does. A year later the man returns to the physician for a blood test. The results of the test show that he has an LDL level of 118 mg/dl, HDL level of 48 mg/dl and a cholesterol level of 161 mg/dl. The man continues taking the atorvastatin for a week every two months for the rest of his life, with his LDL levels ranging from 115-120, HDL levels ranging from 45-51 and his cholesterol levels ranging from 151-162. Based on these results, the once monthly administration of atorvastatin was successful at maintaining normal levels of LDL, HDL and cholesterol.

Example 3

Periodic Treatment with a Statin

A 51 year old male visits his physician and during the visit undergoes a blood test. The man is found to have an LDL level of 87 mg/dl, HDL level of 41 mg/dl and a cholesterol level of 266 mg/dl. The physician prescribes fluvastatin at an initial dose of 60 mg taken orally for a week followed by a two month break where he does not take fluvastatin and then a week of taking fluvastatin followed by a two month break, with this schedule repeated by the man. To remind the man to take fluvastatin following the two month breaks, the physician inputs the days that the man is to take fluvastatin and arranges for the man to receive text messages through Skype that the man will receive on his cell phone and his personal computer. Two months after taking the first weeks dose of atorvastatin, the man receives a reminder by text to take the second weeks dose of atorvastatin two months later. This repeats every two months. The 51 year old man returns to the physician for a follow on blood test six months later and he is found to have LDL level of 112 mg/dl, HDL level of 47 mg/dl and a cholesterol level of 188 mg/dl. At this point the physician changes the frequency of dosing to one week taking fluvastatin followed by a break of three months at a dose of 40 mg, with this schedule repeating thereafter. The physician inputs the new schedule so that the man receives text messages every three months to restart taking fluvastatin. A year later, the man returns to the physician for a blood test. The results of the test show that he has an LDL level of 118 mg/dl, HDL level of 47 mg/dl and a cholesterol level of 179 mg/dl. The physician recommends that the man continue to take fluvastatin for a week followed by a three month break and repeating this schedule thereafter, which the man does. A year later the man returns to the physician for a blood test. The results of the test show that he has an LDL level of 118 mg/dl, HDL level of 48 mg/dl and a cholesterol level of 175 mg/dl. The man continues taking the atorvastatin for a week followed by a three month break and repeating this schedule for the rest of his life, with his LDL levels ranging from 115-120, HDL levels ranging from 45-51 and his cholesterol levels ranging from 151-162. Based on these results, the once monthly administration of atorvastatin was successful at maintaining normal levels of LDL, HDL and cholesterol.

Example 4

Periodic Treatment with a Statin

A 60 year old female visits her physician and during the visit undergoes a blood test. The woman is found to have an LDL level of 91 mg/dl, HDL level of 40 mg/dl and a cholesterol level of 222 mg/dl. The physician prescribes lovastatin at an initial dose of 40 mg taken for a week followed by a break of four months where she does not take lovastatin and this schedule is to be repeated thereafter. To remind the woman to take lovastatin after each four month break, the physician inputs the days that the woman is to take lovastatin and arranges for the woman to receive a letter by postal mail to remind her to take the lovastatin. Four months after taking the first weeks dose of lovastatin, the woman receives a reminder by postal mail to take the second weeks dose. This repeats on an every four month basis. The 60 year old woman returns to the physician for a follow on blood test one year later and she is found to have LDL level of 109 mg/dl, HDL level of 45 mg/dl and a cholesterol level of 184 mg/dl. The woman continues taking the atorvastatin for a week followed by a break of four months, which she repeats for the rest of her life, with his LDL levels ranging from 115-120, HDL levels ranging from 45-51 and his cholesterol levels ranging from 151-162. Based on these results, the once every four month administration of lovastatin was successful at maintaining normal levels of LDL, HDL and cholesterol.

Example 5

Periodic Treatment with a Fibrate

A 55 year old male visits his physician and during the visit undergoes a blood test. The man is found to have an LDL level of 74 mg/dl, HDL level of 32 mg/dl and a cholesterol level of 311 mg/dl. The physician prescribes gemfibrozil at an initial dose of 600 mg taken orally for one week followed by a one month break, followed by a week of taking gemfibrozil followed by a month break, which schedule is repeated thereafter. To remind the man to take gemfibrozil after the monthly break, the physician inputs the days that the man is to take gemfibrozil and arranges for the man to receive text messages through his cell phone and a telephone call to remind him to take gemfibrozil. One month after taking the first weeks dose of gemfibrozil, the man receives a reminder by text to take the second weeks dose of gemfibrozil. This repeats on a monthly basis. The 55 year old man returns to the physician for a follow on blood test six months later and he is found to have LDL level of 101 mg/dl, HDL level of 41 mg/dl and a cholesterol level of 211 mg/dl. The physician recommends that the man continue to take gemfibrozil for a week followed by a month break, which the man does on a repeated basis. A year later the man returns to the physician for a blood test. The results of the test show that he has an LDL level of 106 mg/dl, HDL level of 44 mg/dl and a cholesterol level of 191 mg/dl. The man continues taking the gemfibrozil for a week followed by a month break where he does not take gemfibrozil for the rest of his life, with his LDL levels ranging from 115-120, HDL levels ranging from 45-51 and his cholesterol levels ranging from 151-162. Based on these results, the once monthly administration of atorvastatin was successful at maintaining normal levels of LDL, HDL and cholesterol.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of reducing or maintaining LDL and/or cholesterol and/or increasing or maintaining HDL levels and/or treating a cardiovascular disease in an individual in need thereof, the method comprising the steps of administering a pharmaceutical composition that comprises one or more fibrates to the individual for i) a first period of time of at least one week where the composition is orally administered at least one time daily followed by ii) a second period of time of at least four weeks where the pharmaceutical composition is not administered to the individual, and iii) repeating steps i) and ii) at least two times.

2. The method according to claim 1 further comprising a step of implementing a service to remind the individual to administer the pharmaceutical composition.

3. The method according to claim 1, wherein the first period of time is one week, and the second period of time is about 5 weeks, about 6 weeks, about 7 weeks, about 8 weeks, about 9 weeks, about 10 weeks, about 11 weeks, about 12 weeks or about 4 months.

4. The method according to claim 1, wherein the one or more fibrates are administered to an individual at a dose in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

5. The method according to claim 1, wherein the one or more fibrates are administered to an individual at a dose of at least 1 mg/day, at least 5 mg/day, at least 10 mg/day, at least 15 mg/day, at least 20 mg/day, at least 25 mg/day, at least 30 mg/day, at least 40 mg/day, at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day.

6. The method according to claim 1, wherein the first period of time of administration is for 1 week followed by the second period of time of 4 weeks where the pharmaceutical composition is not administered to the individual.

7. The method according to claim 1, wherein the steps of administering a pharmaceutical composition to the individual for i) a first period of time followed by ii) a period of time where the pharmaceutical composition is not administered to the individual is repeated as provided in step (iii) at least 2 times, at least 3 times, at least 4 times, at least 5 times, at least 6 times, at least 7 times, at least 8 times, at least 9 times, at least 10 times, at least 12 times, at least 15 times, at least 18 times, at least 20 times, at least 25 times, or at least 30 times.

8. The method according to claim 1, wherein the cardiovascular disease includes a heart failure, a pulmonary infarction, or an aortic aneurysm.

9. The method according to claim 1, wherein the one or more fibrates are Bezafibrate, Ciprofibrate, Clofibrate, Gemfibrozil, Fenofibrate or any combination thereof.

10. The method according to claim 1, wherein the first period of time of administration is for 1 week followed by the second period of time of 8 weeks where the pharmaceutical composition is not administered to the individual.

11. The method according to claim 1, wherein the first period of time of administration is for 2 weeks followed by the second period of time of 8 weeks where the pharmaceutical composition is not administered to the individual.

12. The method according to claim 1, wherein the first period of time of administration is for 1 week followed by the second period of time of 12 weeks where the pharmaceutical composition is not administered to the individual.

13. The method according to claim 1, wherein the first period of time of administration is for 2 weeks followed by the second period of time of 12 weeks where the pharmaceutical composition is not administered to the individual.

14. The method according to claim 1, wherein the first period of time is about two week, and the second period of time is about 5 weeks, about 6 weeks, about 7 weeks, about 8 weeks, about 9 weeks, about 10 weeks, about 11 weeks, about 12 weeks or about 4 months.

15. The method according to claim 1, wherein the composition further comprises one or more therapeutic compounds selected from the group consisting of a statin, niacin, an omega-3 fatty acid or any combination thereof.

16. The method according to claim 15, wherein the statin is Atorvastatin, Cerivastatin, Fluvastatin, Lovastatin, Mevastatin, Pitavastatin, Pravastatin, Rosuvastatin or Simvastatin or any combination thereof.

17. The method according to claim 15, wherein the omega-3 fatty acid is a fish oil, an algal oil, a squid oil, a plant oil, or any combination thereof.

18. The method according to claim 17, wherein the plant oil is an echium oil, a flaxseed oil or any combination thereof.

19. The method according to claim 15, wherein the one or more therapeutic compounds are administered to an individual at a dose in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

20. The method according to claim 15, wherein the one or more therapeutic compounds are administered to an individual at a dose of at least 1 mg/day, at least 5 mg/day, at least 10 mg/day, at least 15 mg/day, at least 20 mg/day, at least 25 mg/day, at least 30 mg/day, at least 40 mg/day, at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day.

\* \* \* \* \*